(12) United States Patent
Van Grinsven et al.

(10) Patent No.: US 10,890,584 B2
(45) Date of Patent: Jan. 12, 2021

(54) DEVICES FOR DETECTING ANALYTES USING THERMAL WAVES AND RELATED METHODS

(71) Applicants: Academisch Ziekenhuis Maastricht, Maastricht (NL); Universiteit Maastricht, Maastricht (NL)

(72) Inventors: Bart Robert Nicolaas Van Grinsven, Heerlen (NL); Thomas Jan Cleij, Elsloo (NL)

(73) Assignee: Academisch Ziekenhuis Maastricht, Maastricht (NL)

( * ) Notice: Subject to any disclaimer, the term of this patent is extended or adjusted under 35 U.S.C. 154(b) by 420 days.

(21) Appl. No.: 15/776,324

(22) PCT Filed: Nov. 3, 2016

(86) PCT No.: PCT/EP2016/076571
§ 371 (c)(1),
(2) Date: May 15, 2018

(87) PCT Pub. No.: WO2017/084885
PCT Pub. Date: May 26, 2017

(65) Prior Publication Data
US 2018/0328924 A1  Nov. 15, 2018

Related U.S. Application Data

(63) Continuation of application No. 15/095,636, filed on Apr. 11, 2016, now Pat. No. 10,139,407.
(Continued)

(30) Foreign Application Priority Data

Nov. 16, 2015  (EP) .................................... 15194837
Mar. 29, 2016  (EP) .................................... 16162550
(Continued)

(51) Int. Cl.
*G01N 33/543*  (2006.01)
*G01N 33/569*  (2006.01)
(Continued)

(52) U.S. Cl.
CPC ....... *G01N 33/56911* (2013.01); *G01N 25/18* (2013.01); *G01N 25/20* (2013.01);
(Continued)

(58) Field of Classification Search
None
See application file for complete search history.

(56) References Cited

U.S. PATENT DOCUMENTS 6,161,028 A   12/2000  Braig et al.
8,932,868 B2   1/2015  Van et al.
(Continued)

FOREIGN PATENT DOCUMENTS

EP    2772753 A1    9/2014
JP    2005345385 A   12/2005
(Continued)

OTHER PUBLICATIONS

European Search Report of copending EP application 15 19 4837 dated Feb. 22, 2016.
(Continued)

*Primary Examiner* — Rebecca M Giere
(74) *Attorney, Agent, or Firm* — TraskBritt

(57) ABSTRACT

A device (100) for detecting an analyte (132) includes a polymer material (112) over a substrate (110); a heat transfer element (114) thermally coupled to the substrate; a temperature modification device (118) thermally coupled to the heat transfer element; a controller (121) to produce a thermal (202) wave emanating from the heat transfer element; a flow cell (122) located and configured to pass a liquid (124) over the polymer material; a temperature sensor (134) to detect a
(Continued)

temperature ($T_2$) of the liquid passing over the polymer material; and a processor (123) to calculate a concentration of an analyte (132) in the liquid based at least in part on a phase shift between the thermal wave at the heat transfer element and an attenuated thermal wave (204) in the liquid. Related methods of forming such a device and detecting analytes are also disclosed.

20 Claims, 23 Drawing Sheets

Related U.S. Application Data

(60) Provisional application No. 62/314,461, filed on Mar. 29, 2016.

(30) Foreign Application Priority Data

Mar. 29, 2016 (EP) ..................................... 16162685
Apr. 11, 2016 (EP) ..................................... 16164636

(51) Int. Cl.
G01N 25/18 (2006.01)
G01N 25/20 (2006.01)
G01N 33/487 (2006.01)

(52) U.S. Cl.
CPC ..... *G01N 33/487* (2013.01); *G01N 33/54373* (2013.01); *G01N 2333/245* (2013.01); *G01N 2333/31* (2013.01)

(56) References Cited

U.S. PATENT DOCUMENTS

| | | |
|---|---|---|
| 9,228,970 B2 | 1/2016 | Van et al. |
| 9,429,539 B2 | 8/2016 | Van et al. |
| 9,435,798 B2 | 9/2016 | Eersels et al. |
| 2003/0059807 A1 | 3/2003 | Roach et al. |
| 2003/0199742 A1 | 10/2003 | Braig et al. |
| 2004/0034291 A1 | 2/2004 | Braig et al. |
| 2004/0087841 A1 | 5/2004 | Braig et al. |
| 2004/0126814 A1 | 7/2004 | Singh et al. |
| 2006/0078999 A1 | 4/2006 | Bell et al. |
| 2009/0281272 A1 | 11/2009 | Yilmaz et al. |
| 2012/0186999 A1 | 7/2012 | Walton et al. |
| 2013/0327656 A1 | 12/2013 | Van et al. |
| 2014/0011198 A1 | 1/2014 | Van Grinsven et al. |
| 2014/0242605 A1 | 8/2014 | Eersels et al. |
| 2015/0219584 A1 | 8/2015 | Van Grinsven et al. |
| 2017/0292949 A1 | 10/2017 | Van et al. |
| 2017/0292950 A1 | 10/2017 | Van et al. |

FOREIGN PATENT DOCUMENTS

| | | |
|---|---|---|
| WO | 00/53086 A1 | 9/2000 |
| WO | 2004/079001 A1 | 9/2004 |
| WO | 2012/076349 A1 | 6/2012 |
| WO | 2017084885 A1 | 5/2017 |

OTHER PUBLICATIONS

Peeters et al, Molecules, 2016, 21, 552, 14 pages; www.mdpi.com/journal/molecules.

Bers et al., Heat-Transfer Resistance Measurement Method (HTM)-Based Cell Detection at Trace Levels Using Progressive Enrichment Approach with Highly Selective Cell-Binding Surface Imprints, Langmuir, Apr. 1, 2014, pp. 3631-3639, vol. 30, No. 12.

Bers et al., Supporting Information HTM-based cell detection at trace levels using a progressive enrichment approach with highly selective cell-binding surface imprints, Langmuir, Apr. 1, 2014, pp. 104, vol. 30, No. 12.

Dickert et al., Synthetic receptors as sensor coatings for molecules and living cells, The Analyst, Jun. 1, 2001, pp. 766-771, vol. 126, No. 6, R S C Publications, GB.

PCT International Search Report and Written Opinion, PCT/EP2016/076571, dated May 4, 2017.

Van Grinsven et al., The Heat-Transfer Method: A Versatile Low-Cost, Label-Free, Fast, and User-Friendly Readout Platform for Biosensor Applications, ACS Applied Materials and Interfaces, Aug. 8, 2014, pp. 13309-13318, vol. 6, No. 16.

PCT International Preliminary Report on Patentability, PCT/EP2016/076561 dated May 22, 2018.

DEVICES FOR DETECTING ANALYTES USING THERMAL WAVES AND RELATED METHODS

TECHNICAL FIELD

Embodiments of the present disclosure relate generally to devices and methods of detecting analytes using polymer materials, such as over a heat sink configured to produce a thermal wave.

BACKGROUND

Molecularly imprinted polymers (MIPs) can be used for detecting chemical substances in complex mixtures. In modern research, these polymers are of increasing interest for bioanalytical applications. Advantages of using these MIPs include easy and cheap production; mechanical, chemical, and thermal stability; reusability; and long shelf life. In recent years, the concept of molecular imprinting has been extended to surface imprinting of thin polymer films with micrometer-sized cells to create so-called "surface imprinted polymers" (SIPs) for the detection of proteins, glycoproteins, plant viruses, human viruses, bacteria, pollen, yeast cells, and even mammalian red blood cells. SIPs are polymeric materials with indentations at the surface, with a form and function matching part of a desired target. SIPs are suitable for bonding with larger objects (e.g., cells, bacteria, etc.), which do not diffuse quickly through pores of an MIP. Imprinting may occur after polymerization by softening the polymer. The detection of cells using biosensors described in literature is conventionally done by gravimetric detection, electronic read-out platforms or micro-fluidic techniques. However, these techniques are often time-consuming, provide difficulties for analysis, or require expensive equipment.

For example, temperature resistance of substrates having MIPs attached thereto based on the concentration of analytes is described in U.S. Patent Application Publication 2014/0011198 A1, "Heat-Transfer Resistance Based Analysis Bioparticles," published Jan. 9, 2014, the entire disclosure of which is hereby incorporated herein by reference.

A low-cost sensor platform providing the capability to differentiate between cells with slight differences in shape, size, and functionalities in functional groups on their surface would be a valuable tool for modern research and industry.

DISCLOSURE

In some embodiments, a device for detecting an analyte includes a substrate having a polymer material formed on a surface thereof; a heat sink thermally coupled to a surface of the substrate opposite the polymer material; a temperature modification device thermally coupled to the heat sink; a controller configured to cause the temperature modification device to produce a thermal wave emanating from the heat sink; and a flow cell located and configured to pass a liquid over the polymer material of the substrate. The device may further include a temperature sensor located and configured to detect a temperature of the liquid passing over the polymer material and a processor configured to calculate a concentration of an analyte in the liquid based at least in part on a phase shift between the thermal wave at the heat sink and an attenuated thermal wave in the liquid.

A method for detecting an analyte includes passing a liquid containing an analyte over a polymer material on a substrate; binding the analyte to the polymer material; providing a thermal wave from a heat sink to the polymer material through the substrate; detecting a temperature of the liquid; and calculating a concentration of the analyte in the liquid based at least in part on a phase shift between the thermal wave produced by the heat sink and an attenuated thermal wave in the liquid.

A method of forming a device for detecting an analyte includes forming a polymer material over a surface of a substrate; thermally coupling a heat sink to a surface of the substrate opposite the polymer material; thermally coupling a temperature modification device to the heat sink; configuring a controller to cause the temperature modification device to produce a thermal wave emanating from the heat sink; configuring a flow cell to pass a liquid over the polymer material of the substrate; configuring a temperature sensor to detect a temperature of the liquid passing over the polymer material; and configuring a processor to calculate a concentration of an analyte in the liquid based at least in part on a phase shift between the thermal wave at the heat sink and an attenuated thermal wave in the liquid.

In some embodiments, a method for characterizing bacteria includes passing a liquid containing an analyte comprising a first bacteria and a second bacteria over and in contact with a polymer material on a substrate. The polymer material is formulated to bind to the first bacteria, and the first bacteria binds to the polymer material with a higher affinity than the second bacteria. A heat transfer property of the polymer material varies based on an amount of the analyte bound thereto. The method further includes binding a portion of the first bacteria and the second bacteria of the analyte to the polymer material, removing at least a portion of the second bacteria from the polymer material, detecting a temperature of the substrate, and calculating a concentration of the first bacteria in the liquid based at least in part on the temperature of the substrate.

In other embodiments, a method for characterizing a liquid comprising bacteria includes passing a liquid containing a first strain of bacteria and at least a second strain of bacteria over and in contact with a polymer material on a substrate. The polymer material is formulated to bind to the first strain of bacteria, and the first bacteria binds to the polymer material with a higher affinity than the at least a second bacteria. A heat transfer property of the polymer material varies based on an amount of material bound thereto. The method further includes binding a portion of the first bacteria and a portion of the at least a second bacteria to the polymer material, washing the polymer material to remove the at least a second bacteria therefrom, passing the liquid over the polymer material after washing the polymer material, washing the polymer material at least a second time to remove the at least a second bacteria therefrom, detecting a temperature of the substrate, and calculating a concentration of the first bacteria in the liquid based at least in part on the temperature of the polymer material.

MODE(S) FOR CARRYING OUT THE INVENTION

The illustrations presented herein are not actual views of any particular device or method, but are merely idealized representations employed to describe example embodiments of the present disclosure. Elements common between figures may retain the same numerical designation.

As used herein, the terms "template molecule" and "template bacteria" respectively refer to molecules or bacteria used to form a molecularly imprinted polymer (MIP) or surface imprinted polymer (SIP). Such MIPs or SIPs can then detect "target molecules" or "binding partners," which have functionality corresponding to the template molecules used to form the MIP or SIP.

As used herein, the term "may" encompasses the word "can," and the term "may be" encompasses the words "is" or "are," depending on context. Furthermore, presence of the word "may" is intended to indicate options for practicing or implementing embodiments of the disclosure, without limitation.

Figure 1:
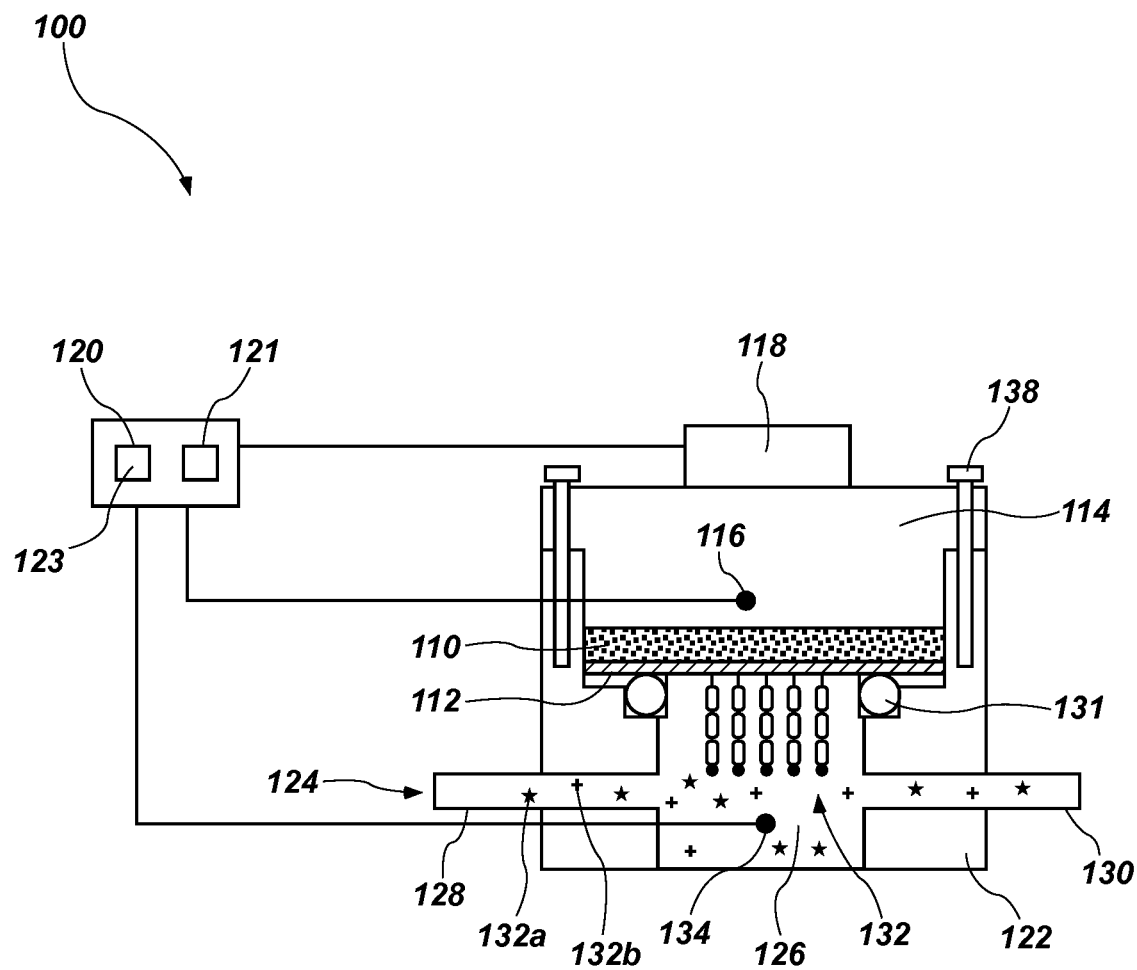
FIG. 1 is a simplified schematic diagram showing a device for detecting an analyte.

FIG. 1 is a simplified schematic diagram showing a device 100 for detecting an analyte. In some embodiments, the device 100 may be configured to detect a target molecule, a nucleic acid such as DNA and/or RNA, single-nucleotide polymorphisms (SNPs) in DNA and/or RNA, small molecules, proteins, bacteria, etc.

The device 100 may include a substrate 110 having a polymer material 112 located over a surface thereof. For example, the polymer material 112 may be formed or disposed over a generally planar surface of the substrate 110, and another, opposite generally planar surface of the substrate 110 may be free of the polymer material 112. In some embodiments, the substrate 110 may include a metal (e.g., aluminum), an alloy, a semiconductor (e.g., silicon, doped diamond, etc.), an electrically insulating material (e.g., undoped diamond). The polymer material 112 may include any material for which a heat transfer property varies based on an amount of the analyte bound thereto. For example, the thermal conductivity, thermal diffusivity, heat capacity, or another property of the polymer material 112 may vary with concentration of the analyte on the surface thereof.

In some embodiments, the polymer material 112 may include an imprinted polymer, such as a molecularly imprinted polymer (MIP) or a surface imprinted polymer (SIP). MIPs and SIPs may also be referred to in the art as "plastic" antibodies. MIPs typically possess a high affinity for a specific binding partner, so that when such binding partners are contacted with the MIP, the molecules bind with the MIP. MIPs are synthetic receptors that contain nanocavities with high affinity for their respective target molecules. Imprinting (i.e., formation of the nanocavities) is often part of the polymerization process. MIPs are able to specifically bind targets, including bacteria, varying from small ions to large cells in complex matrices. Binding of molecules to the MIP may alter some properties of the MIP, such as thermal properties, mechanical properties, electrical properties, etc. The altered property of an MIP may, therefore, be used to detect a presence of such molecules at relatively low concentrations. MIPs are described in, for example, U.S. Patent Application Publication 2009/0281272 A1, "Monodisperse Molecularly Imprinted Polymer Beads," published Nov. 12, 2009, the entire disclosure of which is hereby incorporated herein by reference.

Similarly, SIPs typically possess a high affinity for a specific binding partner, but may typically bind to relatively larger objects (e.g., cells, bacteria, etc.) that do not diffuse quickly through pores of an MIP. SIPs may be polymer materials formed over a surface, then imprinted after polymerization by softening the polymer.

In certain embodiments, the polymer material 112 may include DNA, RNA, proteins, or portions or analogs thereof.

For example, the device 100 may include a substrate 110 (e.g., a diamond surface) functionalized with a polymer material 112 such as DNA, RNA, a protein, a polypeptide, a nucleic acid polymer, a probe, or a portion or analog thereof (e.g., complementary DNA, antibodies, etc.). The polymer material 112 may be formulated to possess a high affinity for a specific binding partner, so that when such binding partners are contacted with the surface of the substrate 110, the molecules bind with the polymer material 112. The polymer material 112 may also bind to analogues of the binding partner (e.g., a material having similar functionality as the binding partner), though not necessarily with the same affinity as binding with the binding partner itself. In some embodiments, the polymer material 112 may include at least about seven (7) repeating units, such as ten (10) repeating units or more.

In some embodiments, the polymer material 112 may include a material screen-printed onto the substrate 110. Screen-printed materials may be manufactured efficiently and in mass quantities, with relatively high uniformity in comparison with other materials.

The device 100 may further include a heat sink 114 thermally coupled to a surface of the substrate 110, such as a surface opposite the polymer material 112. Though referred to as a heat "sink" for the sake of simplicity, the heat sink 114 may be configured to provide heat to or remove heat from the substrate 110 and, so, may also be characterized as a heat transfer element 114. The heat sink or heat transfer element 114 may be a material having a high thermal conductivity, such as a transition metal (e.g., copper, silver, etc.) or an alloy or mixture thereof. In some embodiments, the polymer material 112 may be applied to the heat sink 114 itself. The heat sink 114 may be thermally coupled to a temperature sensor 116 (e.g., a thermocouple or another device) configured to detect a temperature of the heat sink 114, and to a temperature modification device 118 configured to maintain the temperature of the heat sink 114. The temperature modification device 118 may include, for example, a thermoelectric device, a heat exchanger, a fan, a resistance heater, etc. The temperature sensor 116 may be a resistor having a resistance that varies with temperature. If the properties of the heat sink 114 are known (e.g., if a relationship between a control signal to the modification device 118 and the temperature of the heat sink 114 is well characterized), the temperature sensor 116 may be omitted. In some embodiments, the temperature sensor 116 may be integral to the temperature modification device 118. For example, the internal resistance of the temperature modification device 118 itself may be measured to determine its temperature.

The temperature sensor 116 and the temperature modification device 118 may be connected to a controller 121 configured (i.e., programmed) to control the temperature modification device 118 to cause the heat sink 114 to produce a thermal wave emanating from the heat sink 114 and through the substrate 110 (including the polymer material 112 thereon). For example, the controller 121 and a processor 123 may be incorporated into a computer 120 (e.g., the controller 121 may be an input-output card configured to receive and provide electrical signals, and may be configured to receive signals from the processor 123). In some embodiments, the controller 121 may be a proportional-integral-derivative (PID) controller capable of changing the temperature of the heat sink 114 by a small amount on a relatively short time scale. For example, the controller 121 may change the temperature of the heat sink 114 by about 0.5° C. or less, about 0.2° C. or less, or even about 0.05° C. or less. Thus, the thermal wave may have an amplitude of about 1.0° C. or less, about 0.4° C. or less, or even about 0.10° C. or less. The controller 121 may be capable of changing the temperature of the heat sink 114 via the temperature modification device 118 from one set point to another and back to form a thermal wave having a frequency from about 0.001 to about 0.5 Hz, such as from about 0.005 to about 0.1 Hz, or from about 0.01 to about 0.05 Hz. In some embodiments, the controller 121, the temperature modification device 118, and the heat sink 114 may together produce a thermal wave having a variable frequency. Based on a measurement from the temperature sensor 116 (if present), a known input to the temperature modification device 118, or other means, properties of the thermal wave may be known (e.g., a phase, amplitude, frequency at a specific time, rate of frequency change, etc.).

In other embodiments, the controller 121 may be configured to maintain the heat sink 114 at a constant temperature. Detection of analytes using a heat sink at constant temperature is described in U.S. Patent Application Publication 2015/0219584 A1, "Biosensor Using Impedimentric Real-Time Monitoring," published Aug. 6, 2015, the entire disclosure of which is hereby incorporated herein by reference.

The device 100 may further include a flow cell 122 configured to pass a liquid 124 over the polymer material 112 of the substrate 110. The flow cell 122 may define a void 126 adjacent the polymer material 112 of the substrate 110, as well as an inlet 128 and an outlet 130 through which the liquid 124 may flow. An O-ring 131 or another appropriate sealing mechanism may retain the liquid 124 within the flow cell 122 adjacent the polymer material 112 over the substrate 110.

The liquid 124 may include an analyte 132 that specifically binds to the polymer material 112 and change thermal properties thereof, as described above. For example, the analyte 132 may include one or more strains of bacteria. The analyte 132 (which may include multiple analytes 132a and 132b) may specifically bind to the polymer material 112 and changes thermal properties thereof, as described above. If multiple analytes 132a and 132b are present in the liquid 124, the analytes 132a, 132b may have similar functionalities, such that each of the analytes 132a, 132b bind to the polymer material 112. The analytes 132a, 132b may bind to the polymer material 112 with different affinities. In some embodiments, the first analyte 132a may include living bacteria, and the second analyte 132b may include dead bacteria of the same species. In other embodiments, the first analyte 132a may include bacteria, and the second analyte 132b may include an analogue bacteria.

A temperature sensor 134 (e.g., a thermocouple or another device) may be configured to detect a temperature of the liquid 124 in (e.g., flowing through) the flow cell 122. The computer 120 may record the temperature of the liquid 124 by, for example, measuring a resistance of the temperature sensor 134 via the controller 121 and/or the processor 123, and correlating that resistance to a temperature. The temperature of the liquid 124 may be different from the temperature of the heat sink 114, and may vary based at least in part on the presence or absence of the analyte 132 and its concentration in the liquid 124. For example, temperature resistance of substrates based on the concentration of analytes is described in U.S. Patent Application Publication 2014/0011198 A1, "Heat-Transfer Resistance Based Analysis Bioparticles," published Jan. 9, 2014, the entire disclosure of which is hereby incorporated herein by reference.

In some embodiments, the processor 123 may be configured to calculate a concentration of the analyte 132 in the liquid 124 based at least in part on a phase shift between the thermal wave produced by the heat sink 114 and an attenuated thermal wave in the liquid 124 after the thermal wave passes through the substrate 110 and the polymer material 112.

Figure 2:
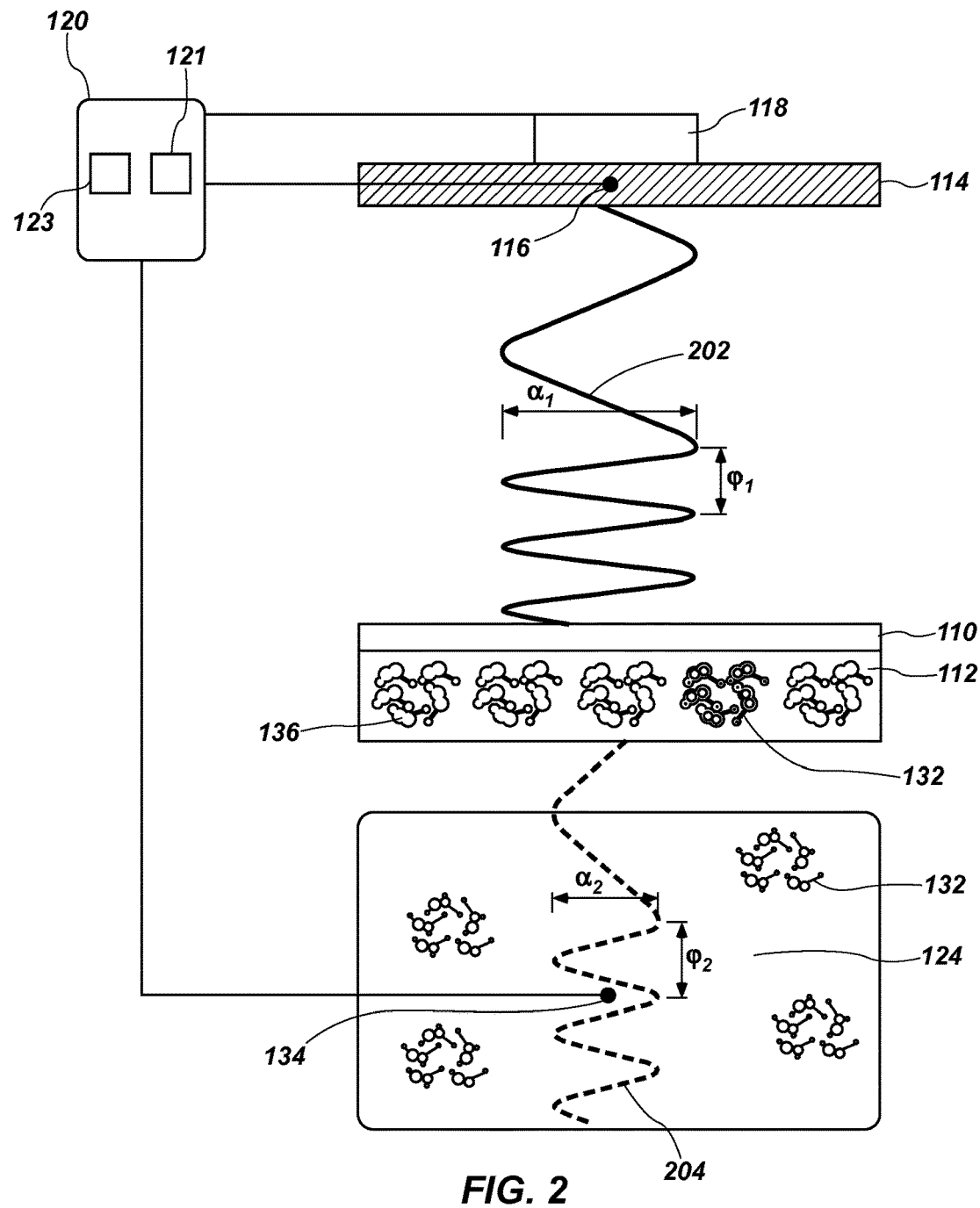
FIG. 2 is a simplified schematic representation showing how a thermal wave may travel in the device of FIG. 1.

FIG. 2 is a simplified schematic representation showing how the thermal wave may travel in the device 100 of FIG. 1. FIG. 2 includes some of the components shown in FIG. 1, but shows them separated to allow representation of thermal waves traveling through and between the components. In particular, FIG. 2 shows the heat sink 114 thermally coupled to the temperature modification device 118 and the temperature sensor 116, which are connected to the computer 120. The concentration of the analyte 132 may be measured based on the differences between the thermal wave at the heat sink 114 and the thermal wave in the liquid 124, without a separate calibration step.

The heat sink 114 may produce a thermal wave 202 and transfer the thermal wave 202 to the substrate 110 and the polymer material 112 thereon. For example, if the heat sink 114 is initially maintained at a constant temperature of 37° C., the thermal wave 202 may be produced by heating the heat sink 114 to a temperature of 37.1° C. and then cooling the heat sink 114 to a temperature of 36.9° C. The heating and cooling of the heat sink 114, driven by the temperature modification device 118, may cause the substrate 110 and the polymer material 112 to heat and cool in a corresponding manner. The thermal wave 202 may have an amplitude $\alpha_1$ and a frequency $\varphi_1$. The amplitude $\alpha_1$ and/or the frequency $\varphi_1$ may vary with time. For example, the thermal wave 202 may have a continuously varying frequency $\varphi_1$.

As discussed above, the presence or absence of the analyte 132 on the substrate 110 may change the thermal conductivity, thermal diffusivity, heat capacity, or another property of the polymer material 112. FIG. 2 illustrates conceptually that the polymer material 112 may define cavities 136 therein adapted to interact with at least a portion of the analyte 132. Without being bound to any particular theory, the cavities 136 may be configured to act to specifically bind the analyte 132. Thus, the polymer material 112 may receive particles or molecules of the analyte 132 from the liquid 124 in some of the cavities 136, based on the concentration of the analyte 132 in the liquid 124. The liquid 124 and the polymer material 112 may reach equilibrium at a given temperature, such that the analyte 132 binds to and separates from the polymer material 112 at equal rates. The thermal properties of the polymer material 112 may depend in part on the fraction of the cavities 136 bound to particles or molecules of the analyte 132.

The substrate 110 and/or the polymer material 112 thereon may alter the thermal wave 202 passing therethrough to form an attenuated thermal wave 204. The attenuated thermal wave 204 may be detected by the temperature sensor 134, and recorded by the computer 120. The attenuated thermal wave 204 may have an amplitude $\alpha_2$ and a frequency $\varphi_2$, which may be different from the amplitude $\alpha_1$ and a frequency $\varphi_1$ of the thermal wave 202. The differences in the amplitudes $\alpha_1$, $\alpha_2$ and/or the frequencies $\varphi_1$, $\varphi_2$ may be correlated to the amount of the analyte 132 bound to the polymer material 112, and thus, to the concentration of the analyte 132 in the liquid 124. Measurement of the differences in the amplitudes $\alpha_1$, $\alpha_2$ and/or the frequencies $\varphi_1$, $\varphi_2$ may allow the device 100 to detect relatively lower amounts of the analyte 132 bound to the polymer material 112 (corresponding to lower concentrations of the analyte 132 in the liquid 124) as compared with conventional methods of measuring the temperature of the liquid 124 at steady state.

In other embodiments, the processor 123 may be configured to calculate a concentration of the analyte 132 based on a steady-state temperature difference between the heat sink 114 and the liquid 124.

Figure 3:
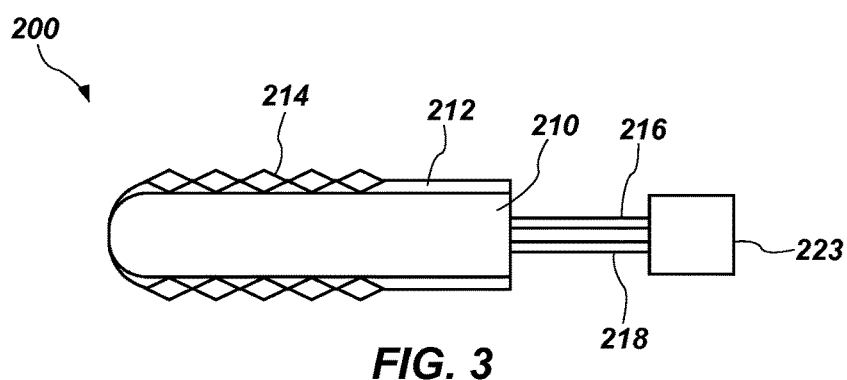
FIG. 3 is a simplified schematic diagram showing another device for detecting an analyte.

In certain embodiments, the analyte 132 may bind to a non-planar surface. For example, FIG. 3 is a simplified schematic diagram showing another device 200 for detecting the analyte 132. The device 200 may include a thermocouple 210 having a base material 212 formed over a surface thereof. For example, the base material 212 may be formed over a generally cylindrical surface of the thermocouple 210, such that an entire end of the thermocouple 210 is enclosed. The thermocouple 210 may include a junction between two materials formulated to provide a temperature-dependent voltage between electrical contacts 216, 218. In some embodiments, the thermocouple 210 may include one or more of a metal (e.g., platinum, gold, iridium, palladium, etc.) or an alloy (e.g., a nickel alloy, a copper alloy, a rhodium alloy, a rhenium alloy, an iron alloy, a molybdenum alloy, etc.).

The base material 212 may be a polymer material such as polylactic-(L)-acid, which may be referred to in the art as PLLA. PLLA is transparent, inexpensive to produce from environmentally renewable sources (e.g., starch or sugar-containing agricultural products), biodegradable, and biocompatible. Furthermore, PLLA can be solubilized in chloroform to enable application to the thermocouple 210. Another material, rather than PLLA, may be selected to be the base material 212, based on desired properties. In some embodiments, the base material 212 may include polyurethane, polylactic acid, polycaprolactone, poly(lactic-co-glycolic acid), poly(D,L-lactide-co-glycolide), or another selected polymer. The base material 212 may be in the form of a thin, smooth, and homogeneous coating over the exterior of the thermocouple 210. Uniformity of the coating by base material 212 may enable to the device 200 to yield reproducible results. The thickness of the base material 212 may be selected in view of the thermal resistance of the base material 212 to affect the rate at which heat may flow toward or away from the thermocouple 210. Thus, a thinner base material 212 may be beneficial for applications in which a fast response is desired or temperature differentials are small.

The base material 212 may be selected to exhibit at least some elasticity, such that the device 200 may be flexible to allow bending of the thermocouple 210 without breaking the base material 212. This may enable the device 200 to be used for applications requiring tight clearance or bends (e.g., in vivo use in catheters).

An assay polymer 214 may be on a surface of the base material 212. In some embodiments, the assay polymer 214 may be directly bonded to the surface of the thermocouple 210, and the base material 212 may be omitted. The assay polymer 214 may include a material for which a heat transfer property varies responsive to an amount of the analyte bound thereto. For example, the thermal conductivity, thermal diffusivity, heat capacity, or another property of the assay polymer 214 may vary with concentration of the analyte on the surface thereof.

In some embodiments, the assay polymer 214 may include an imprinted polymer (an MIP or SIP), DNA, RNA, proteins, or portions or analogs thereof (e.g., antibodies). The assay polymer 214 may be configured to possess a high affinity for a specific binding partner, so that when such binding partners are contacted with the surface of the thermocouple 210, the molecules bind with the assay polymer 214. In some embodiments, the assay polymer 214 may include at least about seven (7) repeating units, such as ten (10) repeating units or more.

In some embodiments, the device 200 may include a processor 223 programmed to calculate an amount of the analyte bound to the assay polymer 214. The processor 223 may calculate a concentration of the analyte in a liquid in contact with the device 200 based at least in part on the amount of the analyte bound to the assay polymer 214. For example, the processor 223 may calculate the amount of the analyte by a method as disclosed in U.S. Patent Application Publication 2014/0011198 A1, "Heat-Transfer Resistance Based Analysis Bioparticles," published Jan. 9, 2014; or U.S. Patent Application Publication 2014/0242605 A1, "Heat-Transfer Resistance Based Analysis of Bioparticles," published Aug. 28, 2014, the entire disclosures of each of which are hereby incorporated herein by reference. In certain embodiments, the processor 223 may be used to detect a phase shift between a thermal wave at or emanating from a heat sink and an attenuated thermal wave at the thermocouple 210. The processor 223 may then calculate the concentration of the analyte in the liquid based at least in part on a difference in amplitude between the thermal wave at the heat sink and the attenuated thermal wave at the thermocouple 210.

Returning again to FIG. 1, the polymer material 112 may be formed or otherwise provided over the substrate 110. For example, the polymer material 112 may be screen-printed onto a metal substrate 110. Screen-printing may be performed efficiently and scaled to produce mass quantities, with relatively high uniformity in comparison with other methods. Screen-printing of substrates is described in, for example, U.S. Patent Application Publication 2012/0186999 A1, "Electrochemical Sensor," published Jul. 26, 2012, the entire disclosure of which is hereby incorporated herein by reference.

The heat sink 114 may be thermally coupled to the substrate 110 at a surface opposite the polymer material 112. For example, the heat sink 114 may be placed in direct physical contact with the substrate 110 such that heat can flow from the heat sink 114 to the substrate 110 by conduction. In some embodiments, a thermally conductive material (e.g., a polymerizable liquid matrix having a thermally conductive filler) may be placed in physical contact with the heat sink 114 and the substrate 110 to eliminate air gaps between the heat sink 114 and the substrate 110. Similarly, the temperature modification device 118 may be thermally coupled to the heat sink 114 by direct physical contact, through a thermally conductive material, or by other appropriate means.

The controller 121 (e.g., a PID controller) may be electrically connected to the temperature modification device 118 to provide power sufficient to drive the temperature of the heat sink 114, and to cause the temperature modification device 118 to change the temperature of the heat sink 114 to produce the thermal wave 202 (FIG. 2).

The flow cell 122 may be secured adjacent the substrate 110 such that the liquid 124 enters the flow cell 122 through the inlet 128, contacts the polymer material 112, and then leaves the flow cell 122 through the outlet 130. In some embodiments, the flow cell 122 may be connected to the heat sink 114 by one or more fasteners 138 (e.g., screws). In other embodiments, the flow cell 122 may be connected to the heat sink 114 by integral threads or by a slip-fit joint. The O-ring 131 or other seal may be configured to keep the liquid 124 from contacting the heat sink 114, the temperature modification device 118, or the back side of the substrate 110 directly.

The temperature sensor 134 may be disposed within the void 126 of the flow cell 122 to measure the temperature of the liquid 124 flowing through the flow cell 122. The temperature sensor 134 may be secured to the flow cell 122 by an adhesive or other appropriate means. The temperature sensor 134 may be electrically connected to the processor 123, which may include an ohmmeter. The processor 123 may be configured to continuously detect the temperature at the temperature sensor 134, and to calculate the concentration of the analyte 132 in the liquid 124 based at least in part on a phase shift between the thermal wave 202 (FIG. 2) produced by the heat sink 114 and the attenuated thermal wave 204 (FIG. 2) in the liquid 124.

The device 100 shown in FIG. 1 and described above may be used to detect any selected analyte 132, such as bacteria. For example, the device 100 may be used for detecting, sensing, and quantifying biological analytes or other chemicals in the liquid 124. The device 100 may be used for detecting, sensing, and quantifying particular strains of bacteria, whether bacteria are living or dead, or discriminating types of bacteria in a complex mixture. The analyte 132 may be a gas, liquid, or solid dissolved or otherwise mixed with the liquid 124. For example, the device 100 may be used for detecting, sensing, quantifying analytes, antibodies, antigens, nucleic acids, (e.g., DNA, RNA, etc.), including nucleic acids with particular sequences (e.g., SNPs), proteins, small molecules (e.g., dopamine, histamine, etc.) or other substances. In some embodiments, the device 100 may be used for detecting histamine, dopamine, serotonin, adrenalin, methylphenidate, etc.

One of the many attractive features of molecular imprinting methods as disclosed herein is that methods can be applied to a diverse range of analytes. The imprinting of small, organic molecules (e.g., pharmaceuticals, pesticides, amino acids and peptides, nucleotide bases, steroids, sugars, etc.) is described in, for example, K. Haupt and K. Mosbach, "Molecularly Imprinted Polymers and Their Use in Biomimetic Sensors," S 100, 2495-2504 (2000); and G. Mustafa and P. Lieberzeit, "MIP Sensors on the Way to Real-World Applications," in *Springer Series on Chemical Sensors and Biosensors*, vol. 12, pp. 167-187 (Springer, 2012). Somewhat larger organic compounds (e.g., peptides) can also be imprinted via similar approaches. Protocols for imprinting larger structures, such as proteins, cells, and mineral crystals have been proposed in, for example, M. Kempe, M. Glad, and K. Mosbach, "An Approach Towards Surface Imprinting Using the Enzyme Ribonuclease A," *J. Molecular Recognition,* 8, 35-39 (1995); S. Hjerten et al., "Gels Mimicking Antibodies in Their Selective Recognition of Proteins," *Chromatographia* 44, 227-234 (1997); H. Shi et al., "Template-Imprinted Nanostructured Surfaces for Protein Recognition," *Nature* 398, 593-597 (1999); A. Aherne et al. "Bacteria-Mediated Lithography of Polymer Surfaces," *J. Am. Chem. Soc.* 118, 8771-8772 (1996); and S. M. D'Souza, et al., "Directed Nucleation of Calcite at a Crystal-Imprinted Polymer Surface," *Nature* 398, 312-316 (1999). Molecular imprinting as a bridge to drug advanced drug delivery is described in B. Sellergren and C. Allender, "Molecularly Imprinted Polymers: A Bridge to Advanced Drug Delivery," *Advanced Drug Delivery Reviews* 57, 1733-1741 (2005). The entire disclosures of each of the documents cited in this paragraph are hereby incorporated herein by reference.

To detect the analyte 132, the liquid 124 containing the analyte 132 may be passed through the flow cell 122, adjacent and in contact with the polymer material 112 over the substrate 110. The analyte 132 (e.g., particles, molecules, or bacteria) binds to the polymer material 112, changing one or more thermal properties of the polymer material 112. The liquid 124 may flow continuously through the flow cell 122 during detection, or the flow may terminate before detection begins. The thermal wave 202 (FIG. 2) and the attenuated thermal wave 204 may travel through the liquid 124 whether the liquid 124 is flowing or stagnant. The thermal properties of liquid 124 may differ for flowing and stagnant liquids 124, but can be determined based on flow properties. In some embodiments, the flow cell 122 and the liquid 124 therein may be brought to a test temperature before detection of the analyte 132. As discussed above, the polymer material 112 may be a molecularly imprinted polymer formulated to bind a particular analyte 132 of interest.

The thermal wave 202 (FIG. 2) is provided from the heat sink 114 to the polymer material 112 through the substrate 110. The controller 121 (e.g., a PID controller) may change the temperature of the heat sink 114 via the temperature modification device 118, such as by raising the temperature and lowering the temperature of the heat sink 114 by a preselected amount and at a preselected frequency. The change in the temperature of the heat sink 114 may be small enough that the change does not interfere significantly with other measurements that may occur simultaneously. For example, the average temperature of the liquid 124 in the flow cell 122 may be measured even though the temperature of the heat sink 114 is varying, so long as the time scale of the average temperature measurement is longer than the frequency of the variation and/or the amount of the temperature variation is small in comparison with the temperature change induced by the interaction of the analyte 132 with the polymer material 112. In some embodiments, the heat sink 114 may provide a thermal wave 202 having a frequency from about 0.001 to about 0.5 Hz, such as from about 0.005 to about 0.1 Hz, or from about 0.01 to about 0.05 Hz. Furthermore, the frequency of the thermal wave 202 may vary during testing (e.g., the frequency may be continuously varied from a low frequency to a high frequency or vice versa). The thermal wave 202 may have an amplitude of about 1.0° C. or less, about 0.4° C. or less, or even about 0.10° C. or less.

The temperature of the liquid 124 in the flow cell 122 may be tested, and the result may be compared with the temperature of the heat sink 114.

The concentration of the analyte 132 in the liquid 124 may be calculated at least in part on a phase shift between the thermal wave 202 produced by the heat sink 114 and the attenuated thermal wave 204 wave in the liquid 124. A comparison of the thermal wave 202 and the attenuated thermal wave 204 may be performed by the processor 123 based on responses of liquids of known concentration. In some embodiments, the comparison of the thermal wave 202 with the attenuated thermal wave 204 may be based at least in part on the amplitudes the phase shift, or another property.

Measurement of the thermal wave enables measurement of thermal resistance without significantly changing the overall temperature of the polymer material 112. Without being bound to any particular theory, such a measurement appears to be a thermal analog to the measurement of capacitance or inductance in the field of electronics. For example, measuring resistance reveals some information about an electronic device or material, but measuring capacitance or impedance reveals additional information, such as how the device or material responds to a load. Similarly, measuring thermal resistance by the methods disclosed herein can reveal additional information that measuring a steady-state temperature difference cannot.

For example, when applying a thermal wave, different types of information are available in the form of a change in amplitude, frequency and/or phase of the attenuated thermal wave in the liquid upon binding of a target to the receptor. The phase shift may vary based on the frequency of the input. The amount of information provided by a thermal wave is much greater than steady-state analysis, and the information may enable detection or differentiation of a wider variety of materials.

Furthermore, and again without being bound to any particular theory, an increase in thermal mass of the polymer material 112 may occur upon binding of the analyte 132 onto its receptor (i.e., the cavities 136). Before binding of the analyte 132, the cavities 136 may be filled with liquid. Upon binding of the analyte 132 into its receptor, the liquid may be replaced by the analyte 132, thus increasing the thermal mass of the entire transducer system.

In some embodiments, the first analyte 132a may be distinguished from the second analyte 132b by removing the second analyte 132b from the polymer material 112. For example, if the first analyte 132a is living bacteria, and the second analyte 132b is dead bacteria, the dead bacteria may be washed or rinsed from polymer material 112 (e.g., with a buffer), leaving the living bacteria behind. Differences in affinity between the first analyte 132a and the second analyte 132b may facilitate such discrimination. In some embodiments, the first analyte 132a may be the template molecule used to form the polymer material 112, and the second analyte 132b may be a molecule or bacteria having some similar functionality. Therefore the second analyte 132b may bind, at least weakly, to the polymer material 112.

EXAMPLES

Examples 1 through 5 build on aspects of biosensing devices described generally in U.S. Patent Application Publication 2014/0011198 A1, "Heat-Transfer Resistance Based Analysis Bioparticles," published Jan. 9, 2014.

Example 1: Preparation of MIP Having a Template for Detecting Dopamine

Ethylene glycol dimethacrylate (EGDM), methacrylic acid (MAA), dopamine hydrochloride salt (99%), and methanol were purchased from Acros Organics (Loughborough, United Kingdom). Prior to polymerization, the stabilizers in the MAA and EGDM were removed by filtration over alumina. 4,4'-azobis(4-cyanovaleric acid) and serotonin creatinine sulfate monohydrate (98%) were purchased from Sigma-Aldrich (Gillingham, United Kingdom). For the heat-transfer measurements, a 1× phosphate buffered saline (PBS) solution was prepared with Dulbecco tablets obtained from Oxoid Limited (Basingstoke, United Kingdom).

A mixture of MAA (0.54 g, 6.6 mmol), EGDM (2.96 g, 14.9 mmol), and 4,4'-azobis(4-cyanovaleric acid) (65 mg) was dissolved in methanol (3.67 ml) and water (0.57 ml) together with dopamine (0.063 g, 0.33 mmol), the template molecule. This mixture was degassed with $N_2$ and heated to initiate polymerization. To allow full completion of the reaction, the mixture was kept at 65° C. for 12 hours. After polymerization, the bulk polymer was ground and sieved to obtain microparticles having diameters smaller than 10 μm. Dopamine was removed from the MIP powders by continuous extraction with a 50/50 mixture of methanol and water. After 6 hours, the MIP was substantially free of dopamine, as verified by AT-IR spectroscopy with a NICOLET™ 380 FT-IR device from Thermo Scientific (Loughborough, United Kingdom). Subsequently, the MIP powder was dried in an oven for 12 hours at 100° C. A non-imprinted polymer (NIP) was synthesized as a control according to the same method, but without the presence of the dopamine.

Example 2: Testing of MIP for Detecting Dopamine

Figure 4:
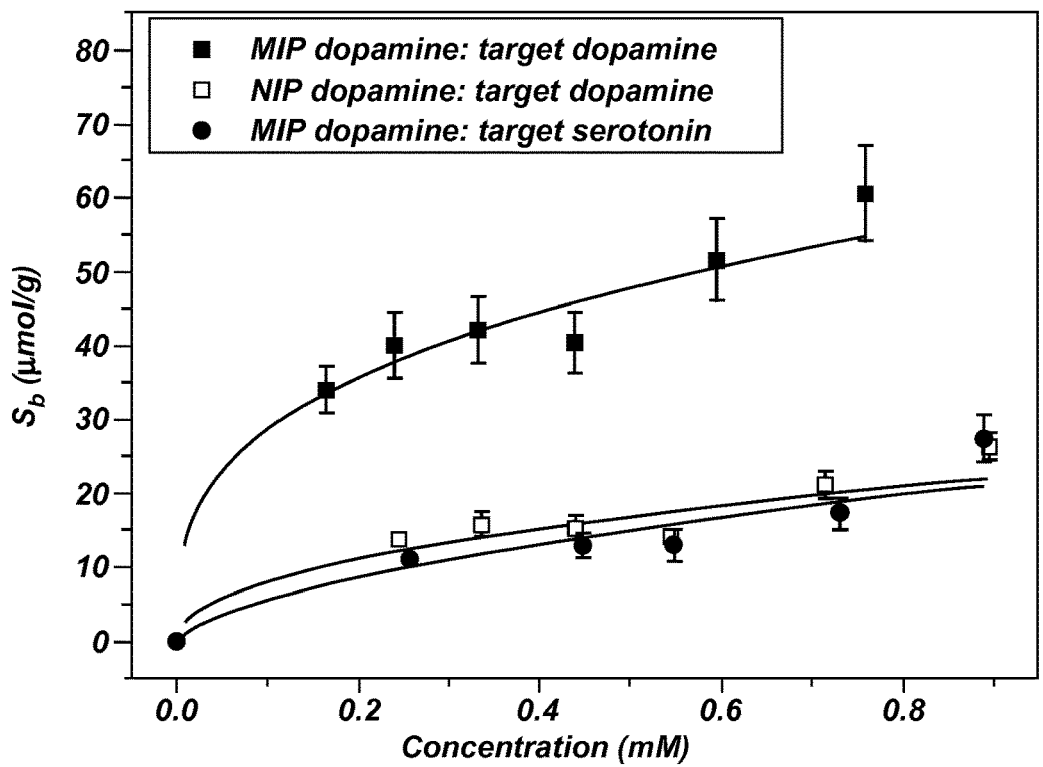
FIG. 4 is a graph showing binding isotherms for dopamine as measured according to an embodiment of the disclosure.

Specificity and binding isotherms of the MIP and NIP particles were determined by optical batch rebinding experiments with an Agilent 8453 spectrophotometer (Stockport, United Kingdom). For the rebinding experiments, 20 mg of MIP or NIP powder was added to 5 ml of aqueous dopamine solutions in concentrations between 0.3 to 1.0 mM. The resulting suspensions were shaken for 12 hours on a rocking table at room temperature. Subsequently, the suspensions were filtered and the free concentration of dopamine ($C_f$) was determined by UV-vis spectroscopy. The bound concentrations ($S_b$) of dopamine were calculated per gram of MIP and NIP and binding isotherms, and are shown in FIG. 4. By fitting the binding isotherms, the specificity of the MIP toward the template dopamine was determined. To test the selectivity, the competitor molecule serotonin was used, since its structure is very similar to dopamine. For these experiments, 20 mg of MIP powder was added to 5 ml of aqueous serotonin solutions and binding isotherms were determined after filtration of the suspensions.

FIG. 4 shows that there is a significant difference in binding between the MIP and its reference, the NIP. To determine the specificity, the imprint factor (IF) was used, which is the amount bound to the MIP divided by the amount bound to the reference NIP at a selected concentration. The binding isotherms were fitted with a two-parameter fit of the following type to analyze the imprint factor at a specific concentration (Equation 1):

$$S_b = A \cdot C_f^v \qquad \text{Equation 1:}$$

Equation 1 corresponds to the Freundlich isotherm and may be used for fitting of MIP binding isotherms if the distribution of the binding sites and affinity constants are assumed to be heterogeneous. At $C_f$=0.3 mM, the IF was 3.1±0.1, whereas higher concentrations yielded slightly lower IF values (~2.5) due to saturation of the binding sites. The results were comparable to other dopamine MIPs in literature. The response of the MIP to the competitor serotonin was not significantly different than the reference, demonstrating the selectivity of the system.

Example 3: Preparation of MIP-Coated Screen-Printed Electrodes (SPEs

Experiments carried out throughout the following Examples utilize Screen-Printed Electrodes (SPEs) (41 mm×7 mm), which comprise a three-electrode configuration with a 3-mm graphite working electrode, a graphite counter electrode and an Ag/AgCl reference electrode.

SPEs were fabricated with stencil designs to form a 3-mm diameter working electrode, using a screen-printing machine (MicroDEK 1760RS, available from DEK, Weymouth, UK). First, a carbon-graphite ink formulation (C2000802P2, available from Gwent Electronic Materials Ltd, UK) was printed onto a polyester substrate having a thickness of 250 μm. The carbon-graphite ink was cured in a fan-oven at 60° C. for 30 minutes. A dielectric paste (D2070423D5, available from Gwent Electronic Materials Ltd) was printed onto the polyester substrate to cover the connections. The dielectric paste was cured at 60° C. for 30 minutes. The reproducibility of this batch of sensors was found to correspond to less than 4% RSD toward a redox probe, $[Ru(NH_3)]^{2+/3+}$/ 0.1 M KCl, using an edge connector.

The MIPs were incorporated into the ink of the SPEs on the basis of the weight percent of $M_P$ and $M_I$, where $M_P$ is the mass of particulate and $M_I$ is the mass of the ink formulation used in the printing process. For the purposes of these Examples, the weight percent of $M_P$ was 30% and the weight percent of $M_I$ was 70%.

Example 4: Cyclic Voltammetry Measurements of SPEs

Figure 5:
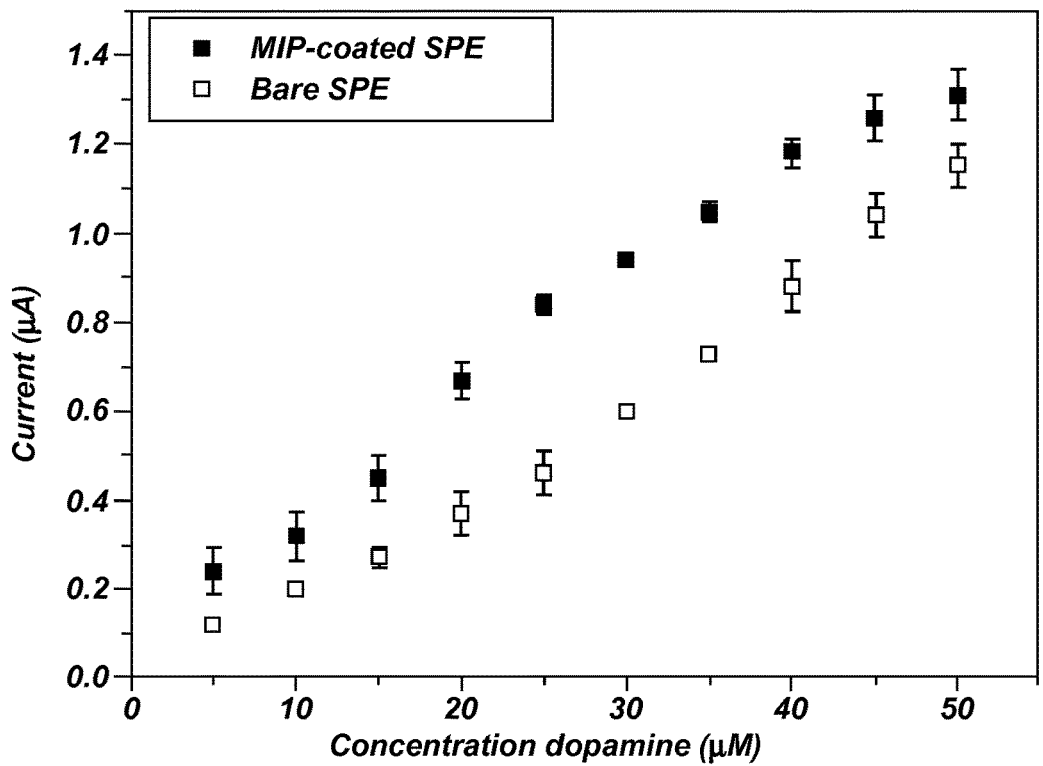
FIG. 5 is a graph showing calibration curves for dopamine as measured according to an embodiment of the disclosure.

Cyclic voltammetric measurements were carried out using a potentiostat (Autolab PG-STAT, available from Metrohm, Utrecht, The Netherlands), using three electrodes. Graphitic screen-printed electrodes and MIP-coated SPEs as described in Example 3 were used as the defined working electrodes. A platinum counter and a saturated calomel electrode (SCE) as the reference electrode complete the circuit. This electroanalytical protocol was studied over a range of dopamine concentrations from 0 to 50 μM, in steps of 5 μM, within a nitrogen-degassed pH-7.4 phosphate-buffered saline (PBS) solution. The oxidation peak at +0.20 V was used as the analytical parameter. This experimental procedure was carried out over the potential range from −0.2 V to +0.8 V at a scan rate of 50 mV/sec. The resulting calibration curves are shown in FIG. 5. Analysis of the oxidation peak height versus dopamine concentration shows that the response in both electrodes was approximately linear.

The response of both electrodes to dopamine can be represented with a linear fit ($R^2$=0.97), indicating the sensitive regime of the sensor platform. For the bare SPEs, the gradient was 0.023 ρA/μM dopamine, while for the MIP-modified SPE the gradient was 0.025 ρA/μM dopamine. The limit of detection was defined as the concentration at which the signal is three times the standard deviation. The limit of detection was 4.7±0.05 μM for the MIP-coated SPE and 4.0±0.06 μM for the bare SPE.

Example 5: Heat-Transfer Method (HTM)

A flow cell having an inside diameter of 6 mm and a height of 4 mm, with a total interior volume of 110 μl, was made of acrylic (available under the trademark PERSPEX®, from Lucite International, of Lancashire, United Kingdom). The flow cell was coupled to the potentiostat system described in Example 4, and was sealed with an O-ring. The contact area between the flow cell and the potentiostat system was 28 mm². The MIP-coated SPEs (described in Example 3) were mounted horizontally and pressed mechanically onto a copper block, which served as a heat sink. The temperature $T_1$ of the copper block was actively controlled by a proportional-integral-derivative (PID) controller with control parameters P=8, I=1, and D=0, and measured by a thermocouple. The temperature $T_1$ of the copper block was maintained at 37.00° C.

A second thermocouple was positioned above the surface of the MIP-coated SPEs, which measured the temperature $T_2$ in the liquid. The thermal resistance, abbreviated as $R_{th}$ (° C./W), was determined by dividing the temperature difference ($T_1$−$T_2$) by the input power P (in Watts) consumed while keeping the temperature constant at 37.00° C. (Equation 2).

$$R_{th} = \frac{T_1 - T_2}{P}.$$ Equation 2

The MIP-coated SPEs were stabilized in phosphate-buffered saline (PBS) solutions, and then increasing concentrations of dopamine (0 to 900 nM) in the solution were added to the flow cell. After stabilization of the signal, the $R_{th}$ values at each concentration were determined. Corresponding dose-response curves were constructed, and are shown in FIG. 4.

Figure 6:
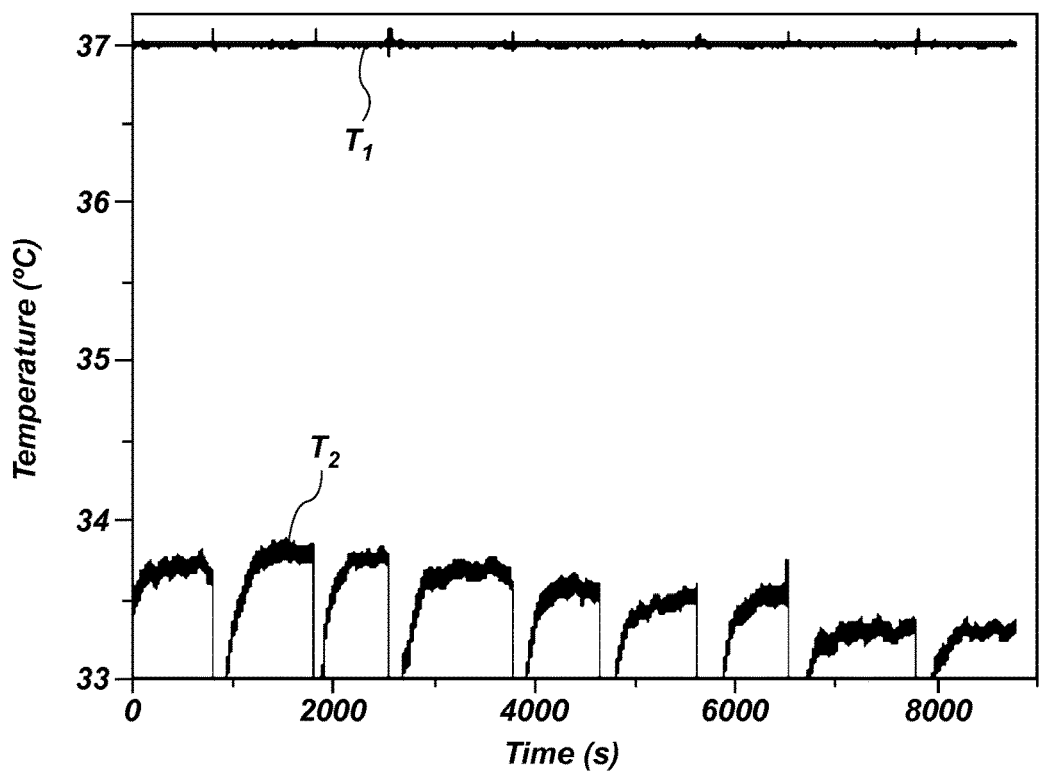
FIG. 6 is a graph showing changes in temperature as measured according to an embodiment of the disclosure.
Figure 7:
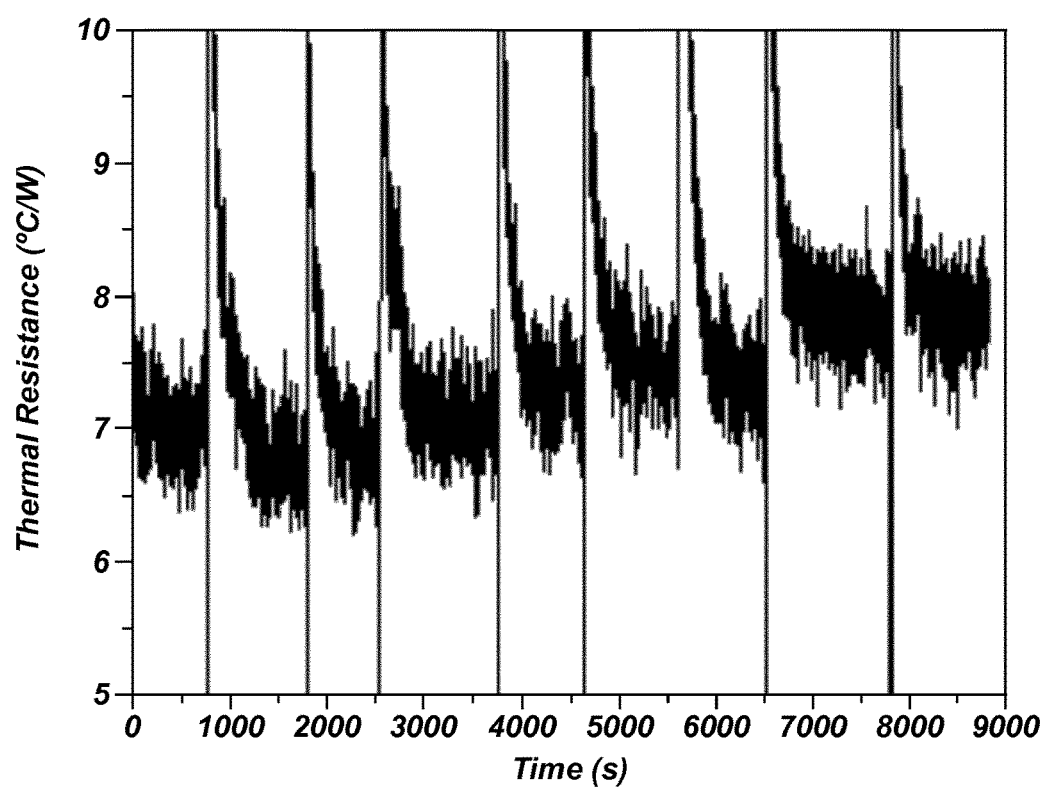
FIG. 7 is a graph showing time-dependent values of thermal resistance as measured according to an embodiment of the disclosure.
Figure 8:
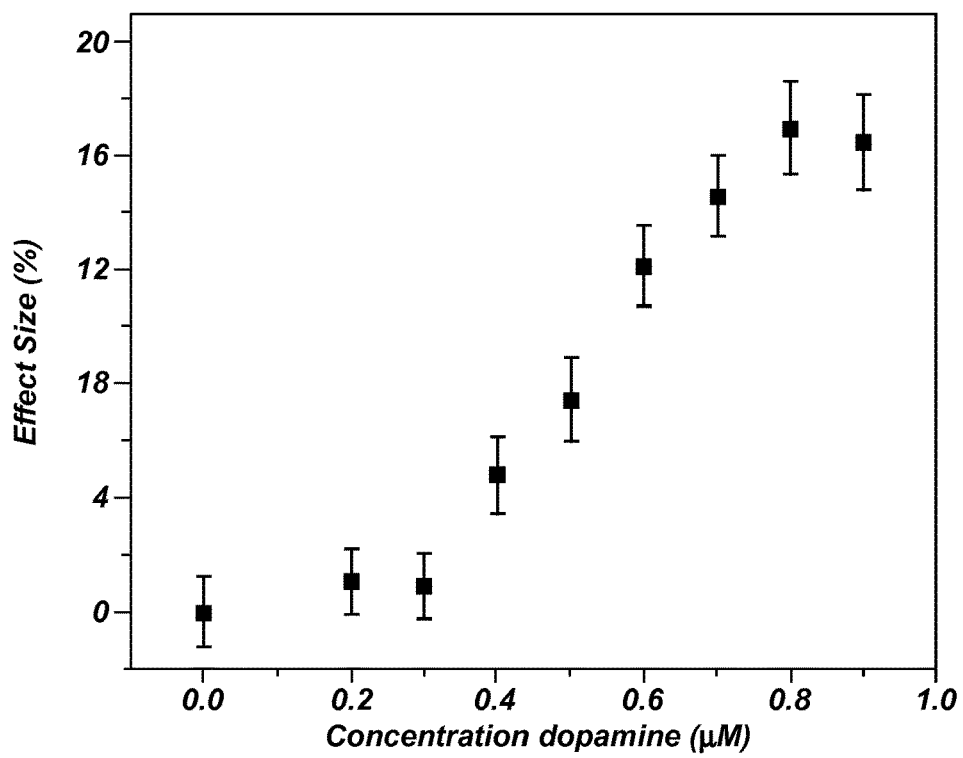
FIG. 8 is a graph showing the thermal resistance data of FIG. 7 in the form of a dose-response curve.

The flow cell was placed in an environment with a stable ambient temperature of 20.00±0.02° C. The temperature of the copper block, $T_1$, was strictly controlled at 37.00±0.02° C. by a PID controller. The flow cell was filled with pure PBS solution; after stabilization of $T_2$, increasing concentrations of dopamine in PBS solutions were added (0 to 1000 nM). As shown in FIG. 6, a change in the concentration of the solution flowing into the flow cell resulted in a quick drop in $T_2$. After reaching a stable plateau level, the sensor cell was left to stabilize for at least 15 minutes. The decrease in $T_2$ can then be solely attributed to the binding of the target molecules to the MIP layer. FIG. 7 shows the time-dependent thermal resistance values, and FIG. 8 shows the corresponding $R_{th}$ data in the form of a dose-response curve. The normalized values shown in FIG. 8 were calculated by dividing $R_{th}$ observed after each addition to the base-line signal.

FIG. 7 illustrates that the thermal resistance $R_{th}$ increased stepwise from 6.80±0.10° C./W to 7.92±0.09° C./W by gradually increasing the dopamine concentration to 900 nM in PBS. This corresponds to a percentage increase of 16.5%, significantly higher than the noise on the signal (1.1%), indicating that the effect is due to binding of the target to the nanocavities of the MIP. When the same test was performed on the reference NIP electrode, the thermal resistance did not significantly change with increasing concentrations of dopamine. Thus, the MIP appears to be specific to dopamine.

As shown in the calculated dose-response curve in FIG. 8; at concentrations up to 800 nM, the binding effect increased linearly with the concentration. At higher concentrations, a trend toward saturation was exhibited, which may be attributed to increasing occupation of the binding sites. With a linear fit, the limit of detection was determined to be 350±30 nM, which is a significant improvement compared to cyclic voltammetry (having a limit of detection of 4700±50 nM, see Example 4).

Example 6: Thermal Wave Transport Analysis (TWTA

Besides analyzing the heat-transport through the functionalized chip, the phase shift in response to the heat sink was studied simultaneously on the same sample as on which the HTM (Example 5) was performed.

Figure 9:
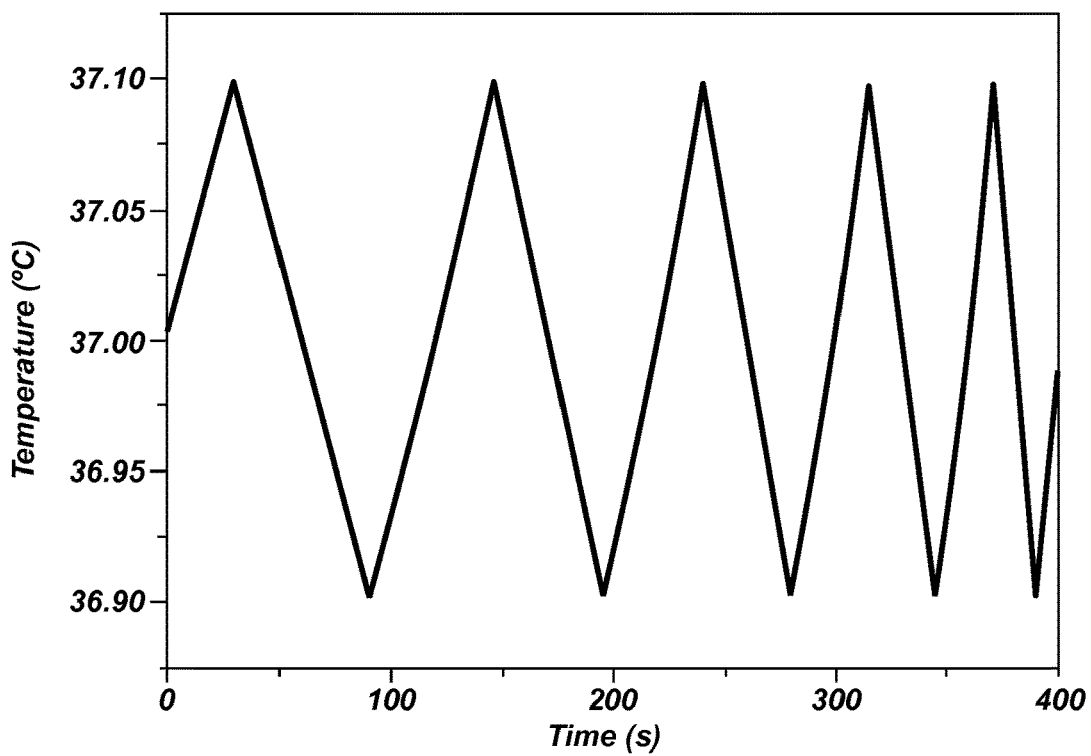
FIG. 9 is a graph showing a thermal wave generated according to an embodiment of the disclosure.
Figure 10:
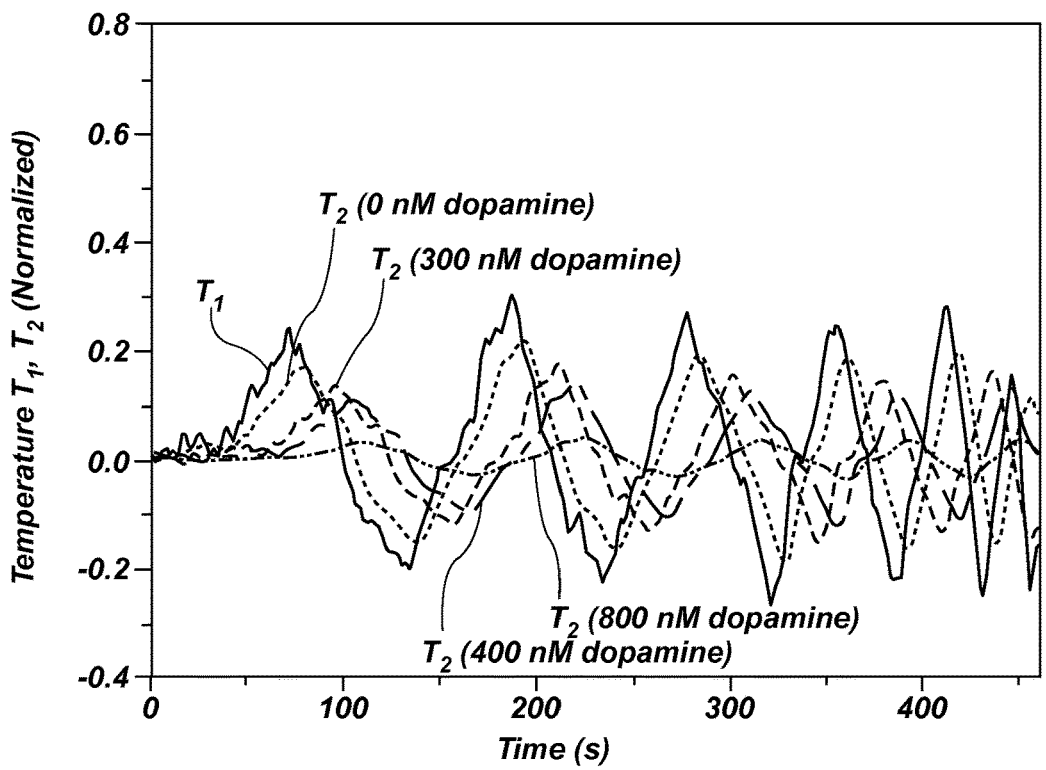
FIG. 10 is a graph showing thermal waves measured after passing through a substrate according to an embodiment of the disclosure.

At four chosen dopamine concentrations in PBS (0, 300 nM, 400 nM, and 800 nM) the PID controller transmitted a thermal wave through the heat sink by a 22-Ωradial leaded high-power resistor (Type MPR Series, available from TE Connectivity, of Schaffhausen, Switzerland) through a thermally conductive silicone paste (SILCOTHERM SG502, available from ACC Silicones Ltd., of Somerset, UK). The thermal wave had an amplitude of 0.1° C. and variable frequency from 0.01 Hz to 0.05 Hz, as shown in FIG. 9. When dopamine was bound to the MIP particles, a delay in the phase ($\varphi_1 \neq \varphi_2$) and a reduction in amplitude ($\alpha_1 \neq \alpha_2$) of the thermal wave output were measured at $T_2$, as shown in FIG. 10. Because the thermal wave had an amplitude of only 0.1° C. and was applied at no more than four distinct points it time, the thermal wave did not affect the stability of the system or the thermal resistance values calculated.

In FIG. 10, the phase shift observed between the input thermal wave ($T_1$) and resulting wave passing through the MIP-coated SPE exposed to a pure PBS buffer solution was due to the time required to transfer heat from the heat sink to the center of the liquid compartment. A slight increase of the phase shift, accompanied with a decrease of the amplitude of the signal, was observed when the MIP-coated SPE was exposed to a 300 nM solution of dopamine in PBS. With higher concentrations of dopamine, the measured phase shift increased more and the amplitude decreased more. Without being bound to any particular theory, it appears that binding of the neurotransmitter to the MIP-layer resulted in a rise in the heat-transfer resistance at the solid-liquid interface. This leads to slower dissipation of the heat from the heat sink to the liquid compartment and appears to explain the results observed in FIG. 10.

Figure 11:
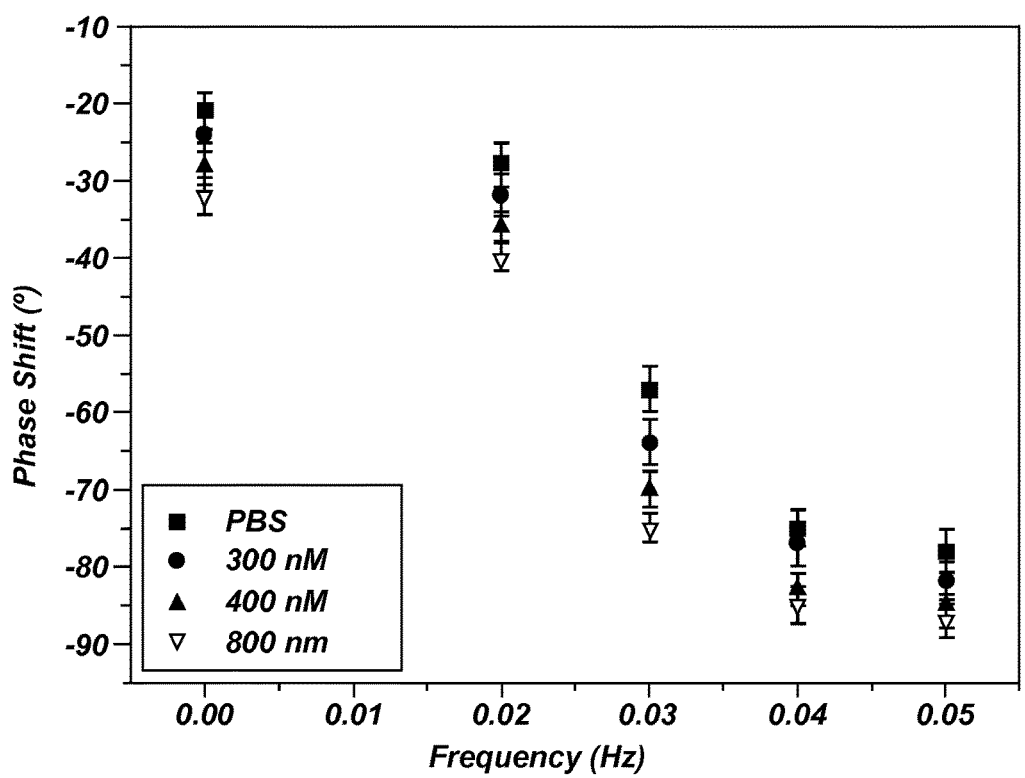
FIG. 11 is a graph showing the phase shift of the thermal waves shown in FIG. 10 as measured according to an embodiment of the disclosure.

FIG. 11 shows the observed phase as a function of the frequency of the applied thermal wave. As shown in FIG. 11, a large change in the phase shift appears between 0.02 Hz and 0.03 Hz, with smaller changes between 0 Hz and 0.02 Hz and between 0.03 Hz and 0.05 Hz. Thus, a frequency of 0.03 Hz was selected to measure target-receptor dynamics in subsequent Examples. At concentrations above 300 nM, a significant effect in the thermal wave output was measured at 0.03 Hz. At this frequency, a phase shift of −57°±1° was observed in PBS, while at 800 nM this increased to −75°±2°, corresponding to a 31%±2% percent increase.

As shown in FIG. 8, the detection limit for dopamine by the heat transfer method (HTM, Example 5) was about 350 mN. However, measuring the phase-shift response, as described in Example 6, dopamine was successfully measured at 300 nM. At a higher concentration of 800 nM, the heat transfer method produced an effect of 16±1%, which is nearly a factor of two lower than for the phase-shift response. Thus, the Thermal Wave Transfer Analysis (TWTA, Example 6) can improve detection of dopamine.

Example 7: Detection of Dopamine in Bananas

Bananas were ground for 4 min in a combined steamer and blender (Avent model SCF870/20, available from Royal Philips, of Eindhoven, The Netherlands) and subsequently centrifuged at 3200 rpm for 5 minutes. The supernatant was filtered to obtain a clear liquid, which was spiked with increasing concentrations of dopamine (62.5, 125, 250, 500, 1000, 2000 nM). At concentrations of 500 nM and higher, a significant effect on the thermal resistance was observed.

Figure 12:
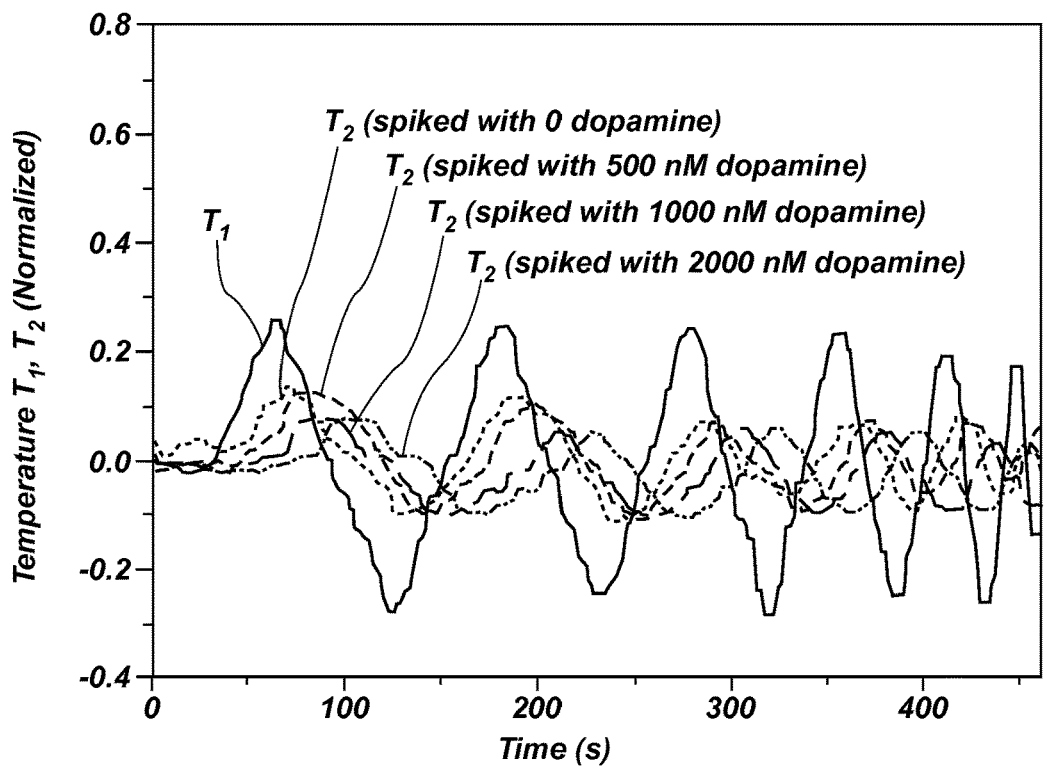
FIG. 12 is a graph showing thermal waves measured after passing through a substrate according to an embodiment of the disclosure.
Figure 13:
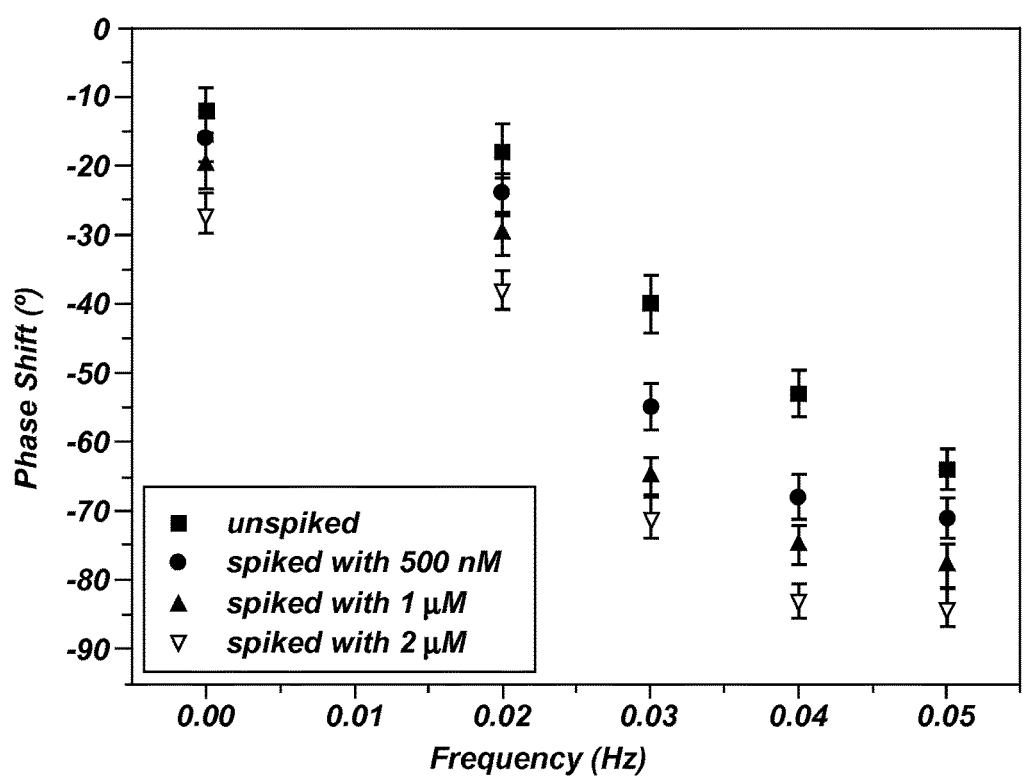
FIG. 13 is a graph showing the phase shift of thermal waves shown in FIG. 12 as measured according to an embodiment of the disclosure.
Figure 14:
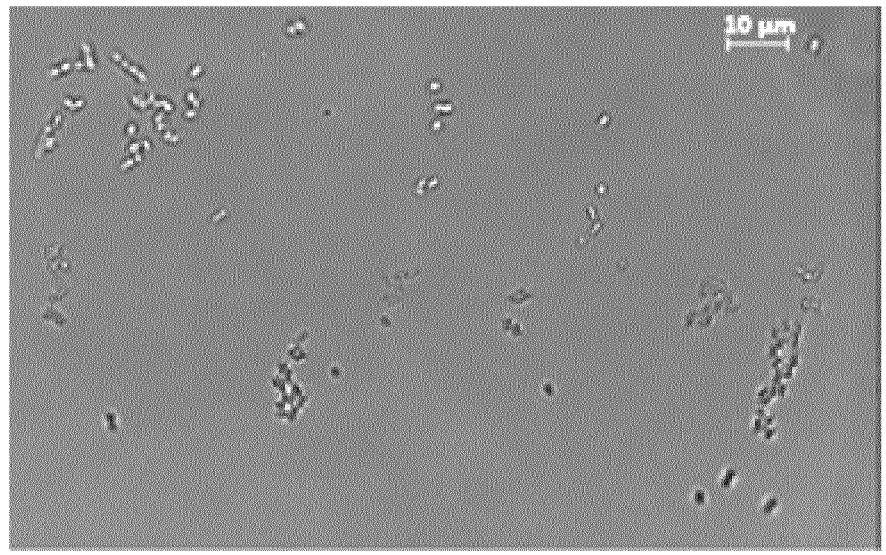
FIGS. 14 and 15 are optical microscopic analyses of polymers imprinted with E. coli and S. aureus, respectively.

The test described in Example 6 was repeated using the banana-derived liquid spiked with dopamine. The result of the thermal wave outputs normalized to the initial temperature of 37.00° C. and corresponding phase shifts are shown in FIG. 12. Only the results for 500 nM and higher concentrations are provided because at lower concentrations no significant difference was observed. A gentle filter (10 point median) was applied to the data to correct for viscosity effects. FIG. 13 shows the observed phase as a function of the frequency of the applied thermal wave. At the spiked concentration of 500 nM, a phase shift of −55±3 Hz was measured compared to 37±2 Hz in a pure, non-spiked solution. In percentage increase, a difference of 46%±2% was measured, which is a combination of the effect of the spiked dopamine concentration and of the initial dopamine present in the banana. Because 500 nM is still in the concentration range in which dopamine is present in biological samples, this Example 7 shows that the Thermal Wave Transfer Analysis (TWTA) technique may be used to measure biologically relevant dopamine concentrations.

Conventional methods are difficult to implement to measure food-related samples because of the high viscosity and the presence of other interfering compounds in food samples, such as large proteins. For example, the limit of detection of certain compounds may increase due to non-specific binding and higher noise levels (compare Example 6, wherein concentrations of 300 nM in buffer were detectable, with Example 7, wherein concentrations of 500 nM were detectable in spiked banana fluid).

Table 1 below compares the detection limits for MIP-modified SPEs of dopamine in buffer solutions and in a food sample. Table 1 shows that thermal methods can provide advantages over conventional electrochemical methods because the limit of detection in buffer solutions is approximately an order of magnitude lower. Furthermore, thermal methods enable measurement of complex food samples. Compared to HTM, analyzing the transport of thermal waves had a significantly higher effect size (31% vs 16% at 800 nM in dopamine buffer solutions) and enhanced the detection limit by requiring less stringent temperature control.

TABLE 1

Detection limits of MIP-modified SPEs of dopamine

| Detection technique | Detection limit of buffer solutions (nM) | Detection limit of food sample spiked with dopamine (nM) |
| --- | --- | --- |
| Cyclic voltammetry | 4700 ± 50 (Example 4) | — |
| Heat-transfer method (HTM) | 350 ± 30 (Example 5) | ~500 nM (Example 7) |
| Thermal wave transport analysis (TWTA) | 300 ± 35 (Example 6) | ~500 nM (Example 7) |

The direct mixing of MIP particles with screen-printing ink may eliminate some steps in preparation of electrodes, and may enable mass-production of functionalized electrodes. Thermal wave transport analysis (TWTA) may result in limits of detection for dopamine in the nanomolar regime for not only buffer solutions, but also with a relevant food sample. An additional benefit is that this technique can be performed simultaneously with the heat-transfer method, allowing direct validation of the results. The described methodology offers a new approach for fast and cost-effective detection of neurotransmitters, which may be used in the fields of biomedical and clinical research.

Example 8: Bacterial Culturing and Sample Preparation

Characterized strains of Escherichia coli (ATCC® 8739™) and Staphylococcus aureus (ATCC® 6538™) were obtained from Leibniz Institute DSMZ, of Braunschweig, Germany. 20 ml of nutrient broth (item number x929.1, from Carl Roth GmbH+Co KG, of Karlsruhe, Germany) was inoculated with a single colony of E. coli. 20 ml of Caso broth (item number x938.1, from Carl Roth) was inoculated with a single colony of S. aureus. Both colonies were allowed to grow overnight at 37° C. while subject to agitation.

1 ml of each overnight culture was diluted in 20 ml of the respective broth, and allowed to grow at 37° C. for 3 hours or until $OD_{600}$ (i.e., optical density measured at a wavelength of 600 nm, a measurement correlated to concentration of the bacteria) of 1 was obtained. Afterwards, the cells were harvested by centrifuging to form pellets, which were washed one time with phosphate buffered saline (PBS), and then resuspended in PBS to achieve desired concentrations.

Example 9: Preparation of Bacteria-Imprinted Polyurethane Layers

A spin-coating solution was prepared by dissolving 122 mg of 4,4'-diisocyanatodiphenylmethane, 222 mg of bisphenol A, and 25 mg of phloroglucinol in 500 μL of anhydrous tetrahydrofuran (THF). All reagents had a purity of at least 99.9% and were used as received from Sigma-Aldrich N.V., of Diegem, Belgium. The solution was polymerized up to its gel point at 65° C. for 200 minutes while gently stirring. The solution was diluted in anhydrous THF in a 1:5 ratio. Polyurethane layers with an average thickness of 1.2±0.1 μm, as measured with a profilometer (Dektak 3ST, Sloan Instruments Corporation, Santa Barbara, Calif., USA) were formed by spin-coating the solution for 60 s at 2000 rpm onto aluminum substrates each having a surface area of 1 $cm^2$.

Polydimethylsiloxane (PDMS) stamps were made using a Dow Corning SYLGARD® 184 silicone elastomer kit purchased from Malvom N.V., of Schelle, Belgium. Bacteria-covered PDMS stamps were formed by applying 400 μL of a bacteria suspension in PBS to each stamp. The bacteria were allowed to settle to the surface of the stamp for 60 s. The excess fluid was removed by spin-coating the stamps at 3000 rpm for 60 s to create a dense monolayer of bacteria on the stamp surface.

The bacteria-covered stamps were each pressed into the polyurethane layer on one of the aluminum substrates at a pressure of 70 Pa. The polyurethane was cured for 18 hours at 65° C. in an inert atmosphere, after which the stamps were removed from the surfaces of the substrates. Template bacteria were washed off with ethanol and PBS, leaving behind selective binding cavities on the surfaces of the substrates. Thus, surface-imprinted polymers (SIPs) were prepared to be selective for each of E. coli and S. aureus.

Example 10: Heat-Transfer Method (HTM)

A flow cell having an inside diameter of 6 mm and a height of 4 mm, with a total interior volume of 110 μl, was made of acrylic (available under the trademark PERSPEX®, from Lucite International, of Lancashire, United Kingdom). The flow cell was coupled to a potentiostat, and was sealed with an O-ring. The contact area between the flow cell and the potentiostat system was 28 $mm^2$. The SIP-coated substrates (described in Example 9) were mounted horizontally and pressed mechanically onto a copper block, which served as a heat sink. The temperature $T_1$ of the copper block was actively controlled by a proportional-integral-derivative (PID) controller with control parameters P=8, I=1, and D=0, and measured by a thermocouple. The temperature $T_1$ of the copper block was maintained at 37.00° C.

A second thermocouple was positioned above the surface of the SIP-coated substrates, which measured the temperature $T_2$ in the liquid. The thermal resistance, abbreviated as $R_{th}$ (° C./W), was determined by dividing the temperature difference ($T_1-T_2$) by the input power P (in Watts) consumed while keeping the temperature constant at 37.00° C., as shown in Equation 2 (see Example 5).

The SIP-coated substrates were stabilized in PBS buffer (pH=7.4) at the beginning of each experiment. Bacteria were introduced to the system by injecting 3 mL of a bacteria solution (1×10$^7$ CFU/mL in PBS) at a controlled flow rate of 2.5 mL/min. The SIP-coated substrates were stabilized, after which the SIP-coated substrates were flushed with PBS at a flow rate of 0.25 mL/min for 12 minutes (total volume 3 mL) to remove any unbound bacteria from the SIP layer. The HTM setup monitors the thermal resistance ($R_{th}$) at the solid-liquid interface at a rate of one measurement per second.

Example 11: Microscopic Imaging

Microscopic imaging of the SIP-coated substrates was performed with a DM750 optical microscope, available from Leica Microsystems, of Diegem, Belgium. The SIP-coated substrates were imaged at magnifications 640× and 1000×. Software (ImageJ version 1.44p, available from National Institutes of Health, Bethesda, Md., USA) was used to determine the number of cell imprints per unit area on microscopic images of the SIP-coated substrates. The average surface coverage of cell imprints was calculated based on cell imprint counts of three different samples for each type of SIP-coated substrate and at five locations on each SIP-coated substrate.

Figure 15:
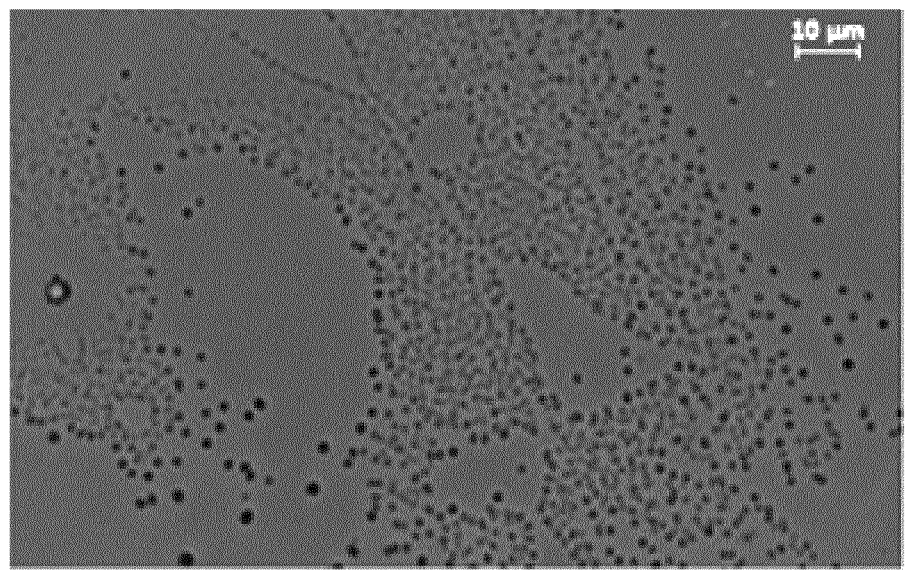

Optical microscopic analysis of a SIP surface imprinted with *E. coli* (FIG. 11) clearly reveals rod-shaped imprints with a length varying from 1.5 to 3 μm and a width of 0.5 to 1.5 μm corresponding to the dimensions of the bacteria. A calculated surface coverage of 1.11×10$^6$±6.62×10$^5$ imprints/cm$^2$ corresponds to a total surface coverage of 6.02±1.6%. Optical microscopic analysis of an *S. aureus* SIP (FIG. 15) shows a heterogeneous distribution of spherical imprints with a diameter of ±500 nm-800 nm. The imprint surface coverage of 2.91×10$^6$±8.73×10$^5$ imprints/cm$^2$ corresponds to a total surface coverage of 9.12±2.1%.

Example 12: Discrimination Between Live and Dead Bacteria

A SIP-coated substrate was formed and imprinted with living *E. coli* cells in PBS (concentration 1×10$^7$ CFU/mL) as described in Examples 8 and 9. The SIP-coated substrate was mechanically pressed with its non-coated, polished backside onto a copper block, to ensure thermal contact between the SIP-coated substrate and the copper block. The SIP-coated substrate was placed in a flow cell, which was filled with PBS. The $R_{th}$ signal of the SIP-coated substrate was allowed to stabilize for 60 minutes. Dead bacteria were introduced into the flow cell for 72 s at a flow rate of 2.5 mL/min. The flow was stopped, and the $R_{th}$ signal was allowed to stabilize for 60 min, allowing the bacteria to sediment towards the SIP surface. Any unbound bacteria were removed by flushing the flow cell with PBS for 12 minutes at a rate of 0.25 mL/min. After a 60-minute stabilization interval, the experiment was repeated with living *E. coli* cells. The results of this experiment are shown in FIGS. 16 and 17.

Figure 16:
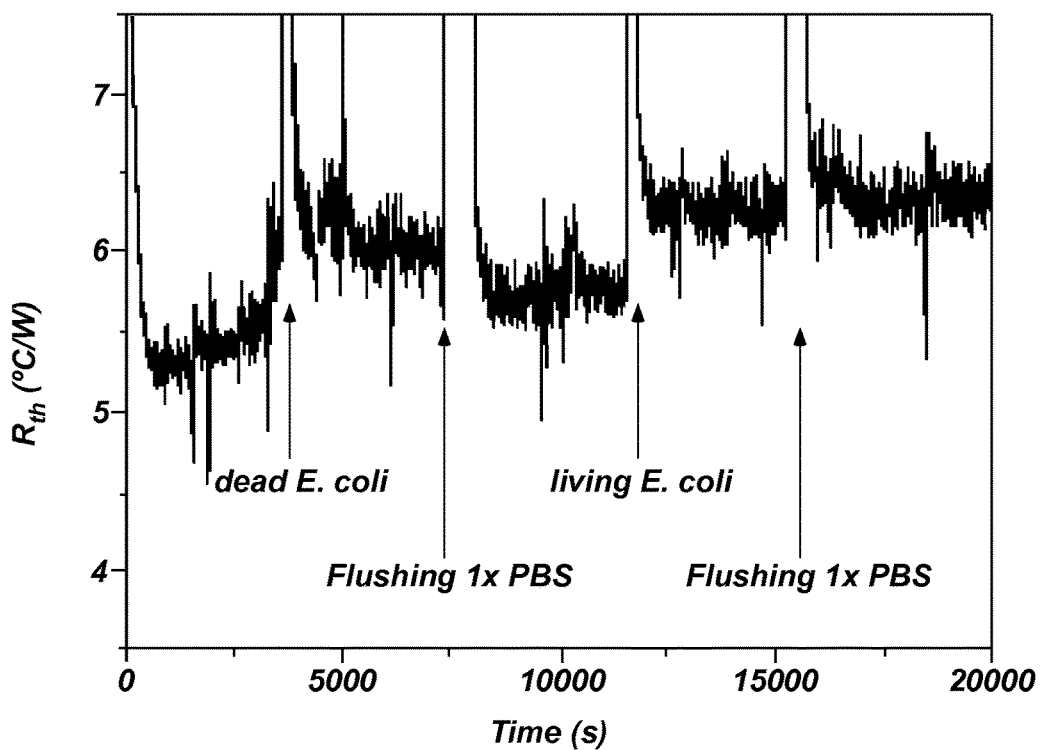
FIG. 16 is a graph showing thermal response of a device alternately exposed to dead and living E. coli, with flushing in between exposures.

FIG. 16 shows that both exposure events (i.e., exposure to living and dead *E. coli* cells) result in an increase in thermal resistance at the solid-liquid interface of the SIP-coated substrate. The increase associated with an addition of dead bacteria can be partially reversed by flushing with PBS, whereas the increase caused by adding living *E. coli* cells appears irreversible. FIG. 17 is a boxplot summarizing the data. Error bars indicate the standard deviation of the noise on the signal.

Figure 17:
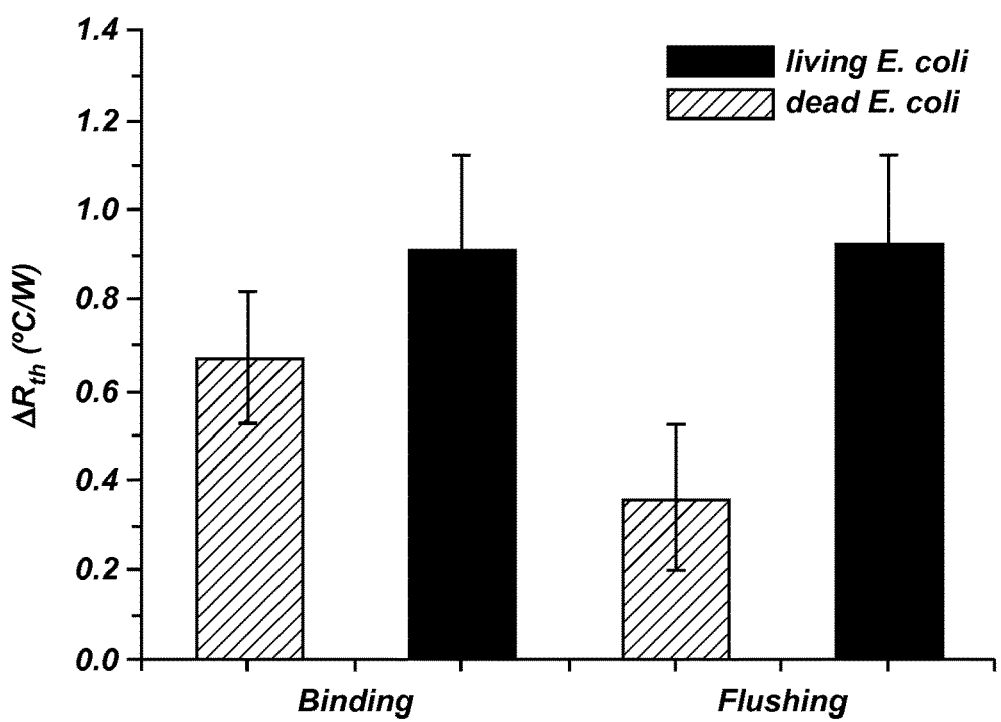
FIG. 17 is a boxplot summarizing the thermal responses shown in FIG. 5.

FIGS. 16 and 17 indicate that the signal ($R_{th}$) increases upon addition of a solution of dead bacteria in PBS by 0.67±0.15° C./W. Upon flushing the chamber with PBS the signal drops back to a value 0.36±0.16° C./W above the baseline. After infusing the live bacteria into the measuring chamber the signal increases again to a value 0.91±0.21° C./W. Flushing with buffer solution does not cause a measurable decrease in $R_{th}$, and the signal remains at 0.93±0.19° C./W above the baseline.

The thermal resistance tests described in Example 12 and in FIGS. 16 and 17 show comparable responses upon initial exposure to dead and living bacteria, although the increase in $R_{th}$ is somewhat lower for dead cells. The morphology of the dead bacteria cells appears to be compatible with the dimensions of microcavities on the imprinted polymer surface. Additionally, dead bacteria express some bacteria-specific functional groups on their outer membranes, which may provide a partial functional match between the dead bacteria and the imprinted surface. Both living and dead cells alter heat flow properties through microcavities of the polymer, typically increasing thermal resistance at the solid-liquid interface. Rinsing the imprinted surface may provide sufficient shear forces to remove the dead bacteria from microcavities on the imprinted surface. Exposure of the imprinted surface to living *E. coli*, on the other hand, may produce an increase in thermal resistance that cannot be reversed by a simple flushing. The bond between the imprints and living bacteria appears to be more stable than the bond between imprints and dead bacteria. Differentiation between dead and living bacteria from the same species may be based on chemical functionalization created within microcavities during imprinting.

Example 13: Selectivity Between *E. coli* and *S. aureus*

SIP-coated substrates were formed and imprinted with *S. aureus* cells (gram-positive bacteria) and *E. coli* cells (gram-negative bacteria) as described in Examples 8 and 9. The SIP-coated substrates were mechanically pressed with their non-coated, polished backsides onto copper blocks, to ensure thermal contact between the SIP-coated substrates and the copper blocks. The SIP-coated substrates were placed in a flow cell, which was filled with PBS. Time-dependent $R_{th}$ data were acquired by consecutively exposing the SIP-coated substrates to analogue non-target bacteria and target bacteria. The flow cell was flushed at a controlled velocity between both exposure events.

Figure 18:
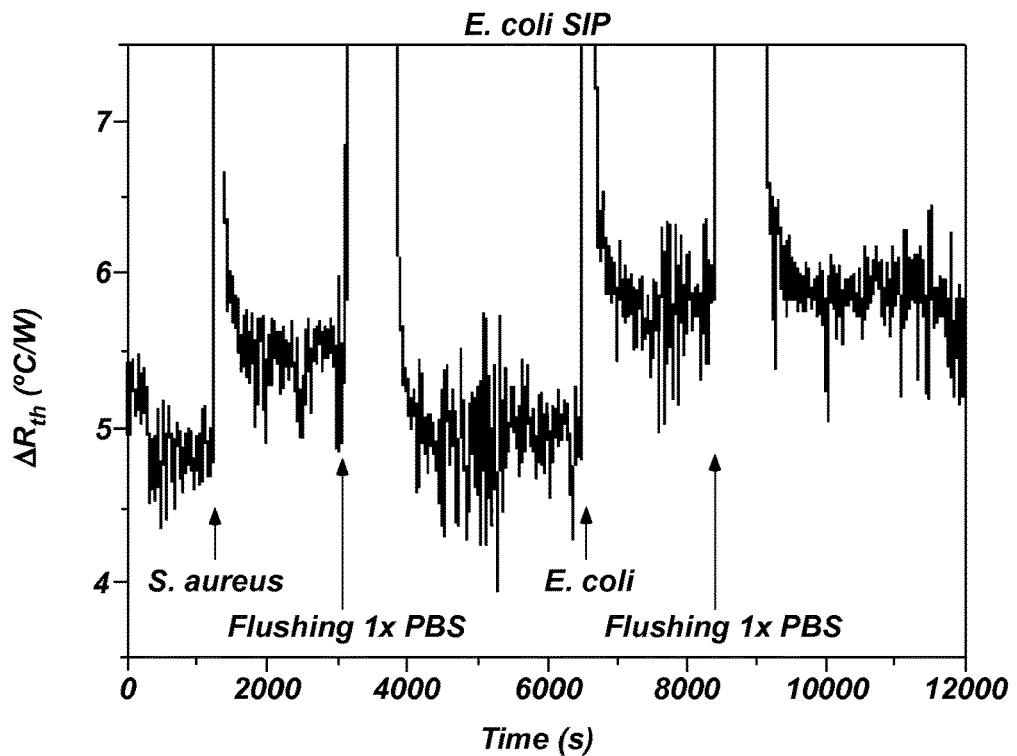
FIGS. 18 and 19 are graphs showing thermal responses of devices alternately exposed to S. aureus and E. coli, with flushing in between exposures.
Figure 19:
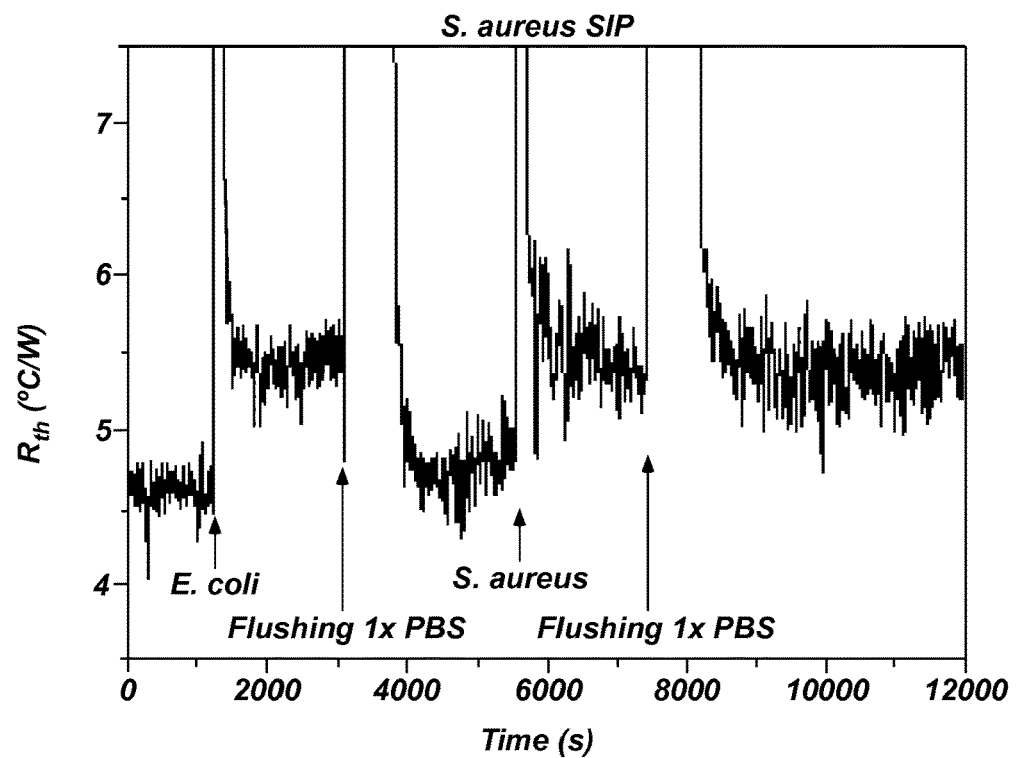

FIG. 18 shows that exposing an *E. coli*-imprinted SIP to a suspension of *S. aureus* cells in PBS (concentration 1×10$^7$ CFU/mL) increased the thermal resistance at the solid-liquid interface with by 0.62±0.14° C./W. Rinsing the flow cell with PBS returned the signal back to baseline ($\Delta R_{th}$=0.07±0.21° C./W). Repeating the cycle with an *E. coli* solution having the same concentration produced an irreversible increase in $R_{th}$ of 0.96±0.16° C./W ($\Delta R_{th}$ upon flushing=0.94±0.12° C./W). A similar trend was observed when exposing an *S. aureus*-imprinted SIP to *E. coli* followed by *S. aureus*, as shown in FIG. 19. Exposure to a solution of *E. coli* cells increased the $R_{th}$ signal with 0.76±0.09° C./W but upon rinsing the flow cell with PBS, the thermal resistance stabilized at a value 0.12±0.11° C./W above the baseline. Exposing the SIP to a solution of target cells, led to an increase in thermal resistance of 0.91±0.17°

C./W. Flushing the cell with PBS did not significantly change the signal (0.87±0.19° C./W).

Figure 20:
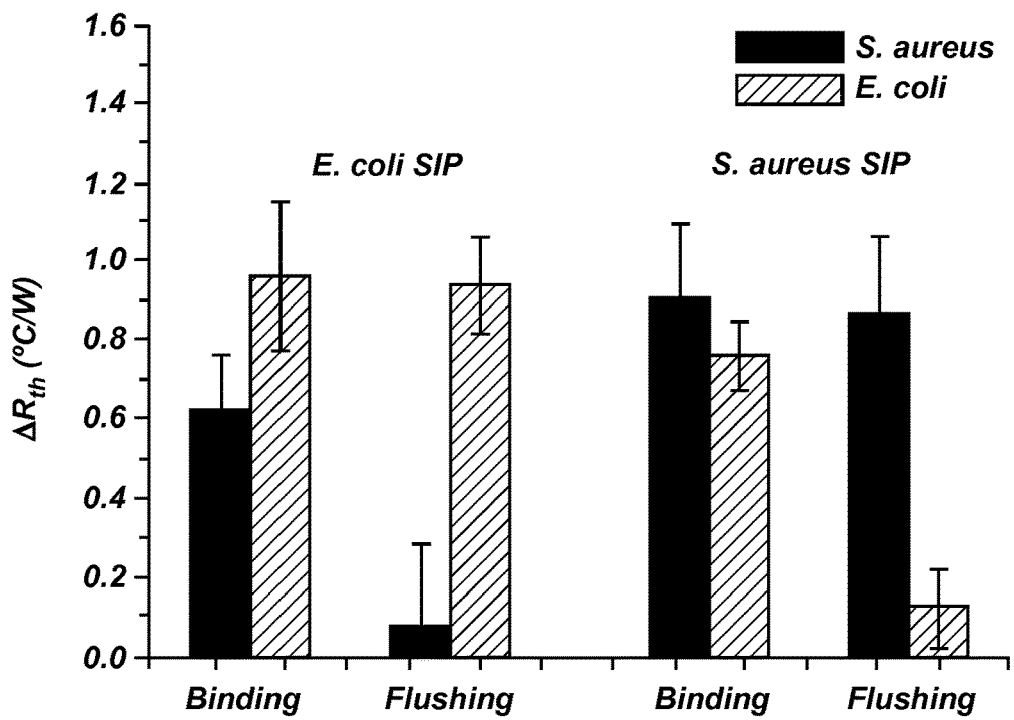
FIG. 20 is a boxplot summarizing the thermal responses shown in FIGS. 7 and 8.

Thus, FIGS. 18 and 19 each shown time-dependent $R_{th}$ measurements of SIPs imprinted with either *E. coli* (FIG. 18) or *S. aureus* (FIG. 19) during consecutive bacterial exposure events to analogue non-target bacteria and finally to target bacteria. In both cases, addition of non-target bacteria species led to an increase in thermal resistance, but the signal returned to near baseline upon flushing the flow cell with buffer solution. Binding of target bacteria to the SIP led to an irreversible rise in $R_{th}$. The results of these experiments are summarized in a box plot in FIG. 20.

Example 14: Sensitivity Test and Dose-Response Curve

Figure 21:
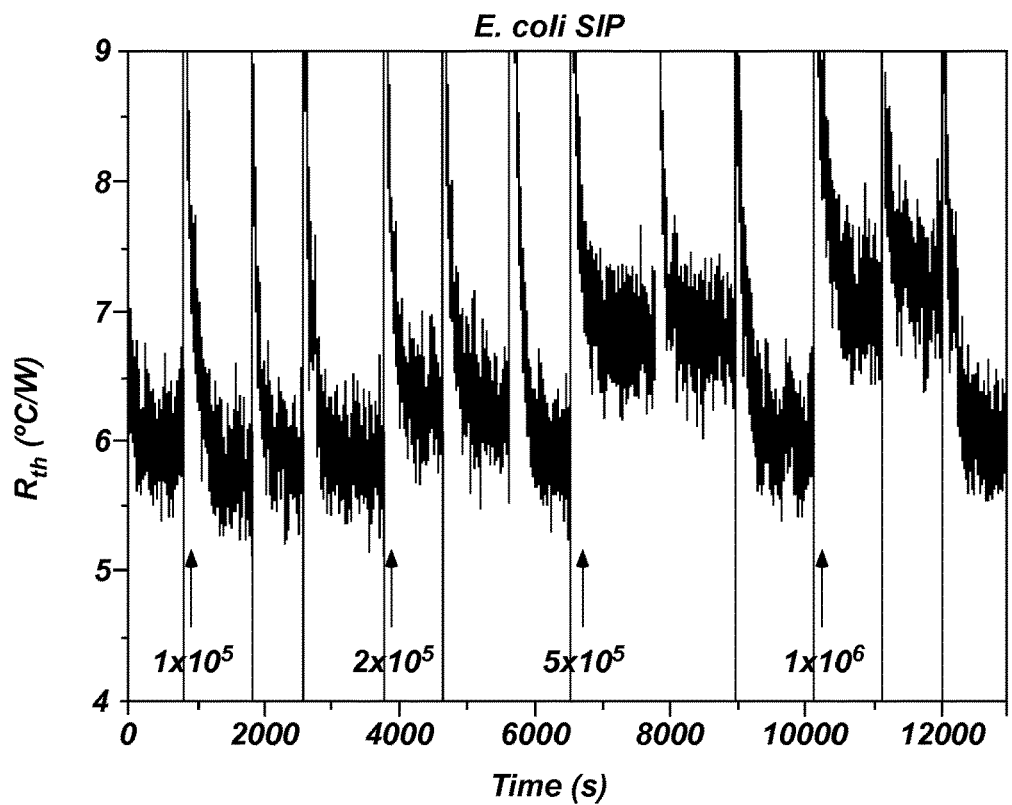
FIG. 21 is a graph showing thermal response of a device exposed to increasing concentrations of E. coli, with flushing in between exposures.

Portions of a stock solution of *E. coli* cells in PBS with a concentration of 1×10$^7$ CFU/mL were diluted 100, 50, 20 and 10 times, and a SIP-coated substrate (imprinted with *E. coli*, as described in Examples 8 and 9) was consecutively exposed to an increasing concentration of target *E. coli* cells in a flow cell. In between each exposure step, the flow cell was rinsed with ethanol for 12 minutes at a rate of 0.25 mL/min, followed by a rinse with PBS for 12 minutes at a rate of 0.25 mL/min. The results of this experiment are shown in FIG. 21. The results identify the limit-of-detection (LoD) of the SIP-coated substrate.

Figure 22:
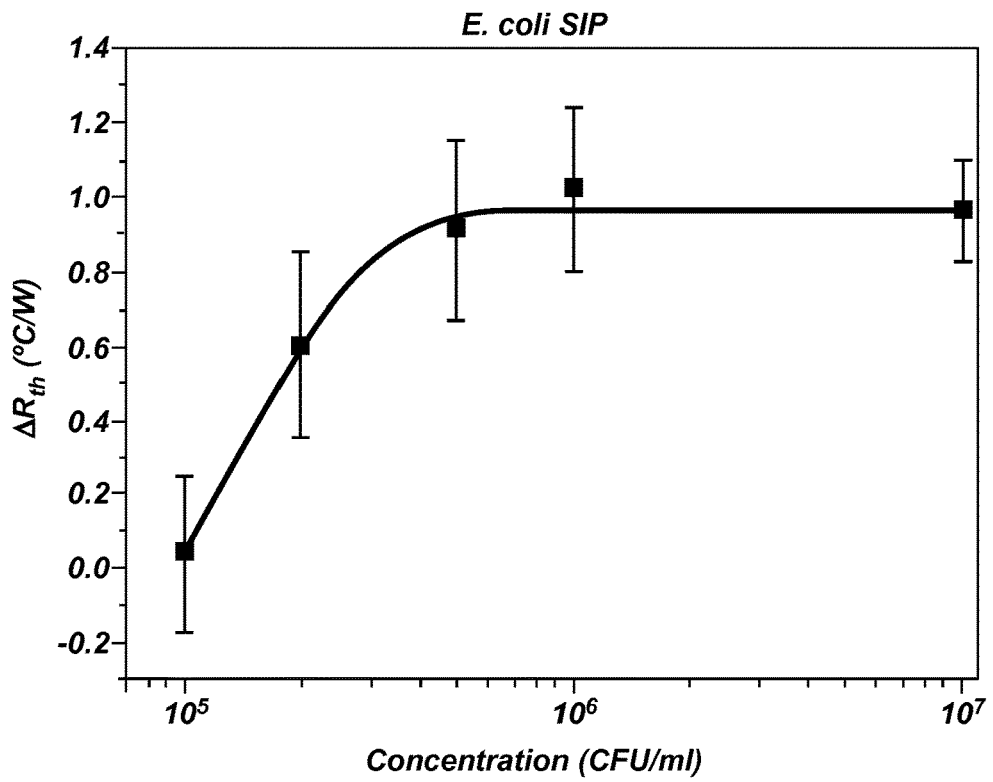
FIG. 22 is a dose-response curve derived from the thermal responses shown in FIG. 10.

The thermal resistance increased when the *E. coli* cells were added, and the increases appear to be concentration-dependent. The time-dependent thermal resistance data shown in FIG. 21 indicate that exposing the SIP-coated substrate to a concentration of 1×10$^5$ CFU/mL did not result in a measurable increase in $R_{th}$. Upon addition of a concentration of 2×10$^5$ CFU/mL, the signal started to increase. The signal appeared to start saturating at a concentration of 5×10$^5$ CFU/mL. These results combined with the results from the previous experiment were used to establish a dose-response curve shown in FIG. 22 showing a response in $R_{th}$ as a function of the added target-bacteria concentration on a logarithmic scale.

The dose-response curve follows an empirical, exponential fit function according to the formula:

$$\Delta R_{th}(c) = A - B \times \exp\left\{-\frac{c}{C}\right\},$$

where c is the concentration of *E. coli*, and A, B, and C are constants. The exponential fit drawn through the obtained data in FIG. 22 has an $R^2$-value of 0.9901.

The sensitivity tests described in Example 14 and FIGS. 21 and 22 reveal that sensors as described herein qualitatively respond to an elevated concentration of target bacteria species in a sample and that the response can be quantified. At relatively low concentrations, the sensor's response may remain within noise levels. But starting from a threshold concentration (about 2×10$^5$ CFU/mL in Example 14), the $R_{th}$ signal increases to a value high enough above the baseline to be statistically distinguishable (indicating that a sufficient amount of cells interacts with and binds to the microcavities on the imprinted polymer, blocking heat flow through the polymer and thereby increasing the heat-transfer resistance). This effect becomes more pronounced with an increasing concentration, but the polymer seems to saturate (at concentrations above 5×10$^5$ CFU/mL in Example 14). Using the exponential fit to the data and defining the detection limit as the concentration at which the signal-to-noise ratio is larger than 3, the limit of detection (LoD) for the sample in Example 14 was 1.5×10$^5$ CFU/mL. The LoD may be affected by, for example, the synthesis protocol for bacterial imprinting, including sedimentation time, spin-coat velocity and acceleration, template concentration, and surface functionalization of the stamp surface. In addition, the noise of the signal may be improved by electronic noise reduction, shielding, insulation, etc.

Example 15: Detection of *E. coli* in a Semi-Complex Matrix

A solution was prepared containing both *E. coli* and *S. aureus* cells in a 1:99 ratio. The total concentration of bacteria was 1×10$^7$ CFU/mL. This mixture was used in a progressive enrichment experiment.

Figure 23:
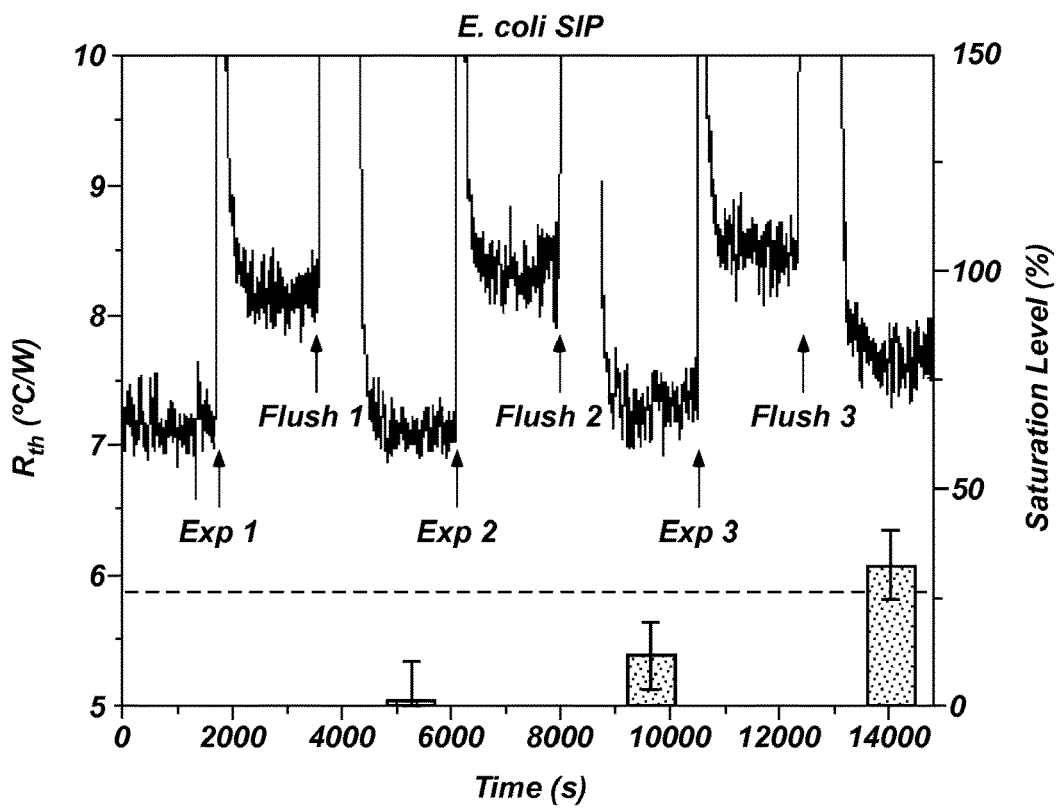
FIG. 23 is a graph showing thermal responses of a device exposed to a mixture of E. coli and S. aureus, with flushing in between exposures, as well as a boxplot summarizing the thermal responses.
Figure 24:
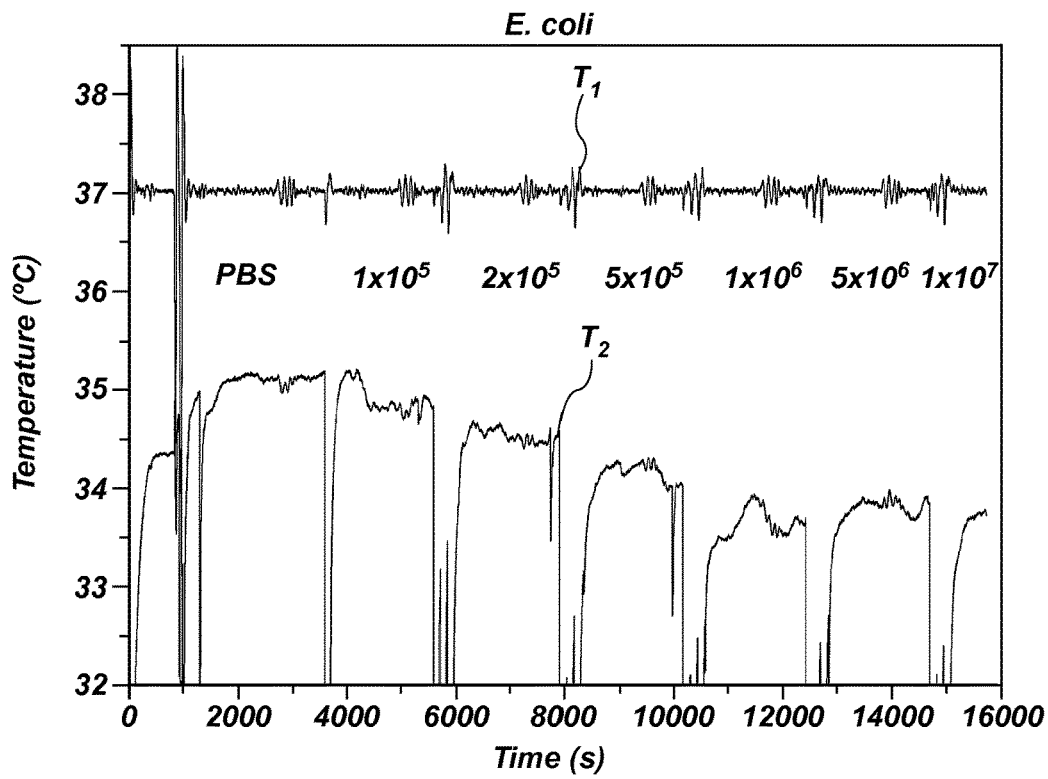
FIGS. 24 through 30 are graphs showing changes in temperature of devices as measured according to an embodiment of the disclosure.
Figure 25:
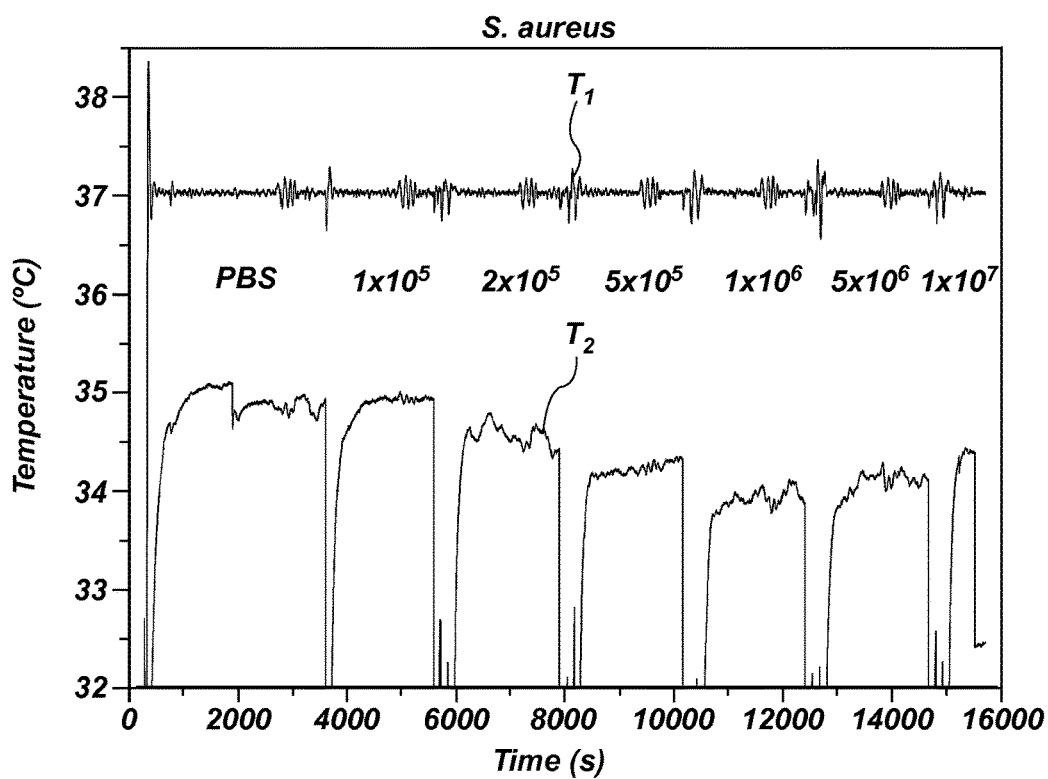
Figure 26:
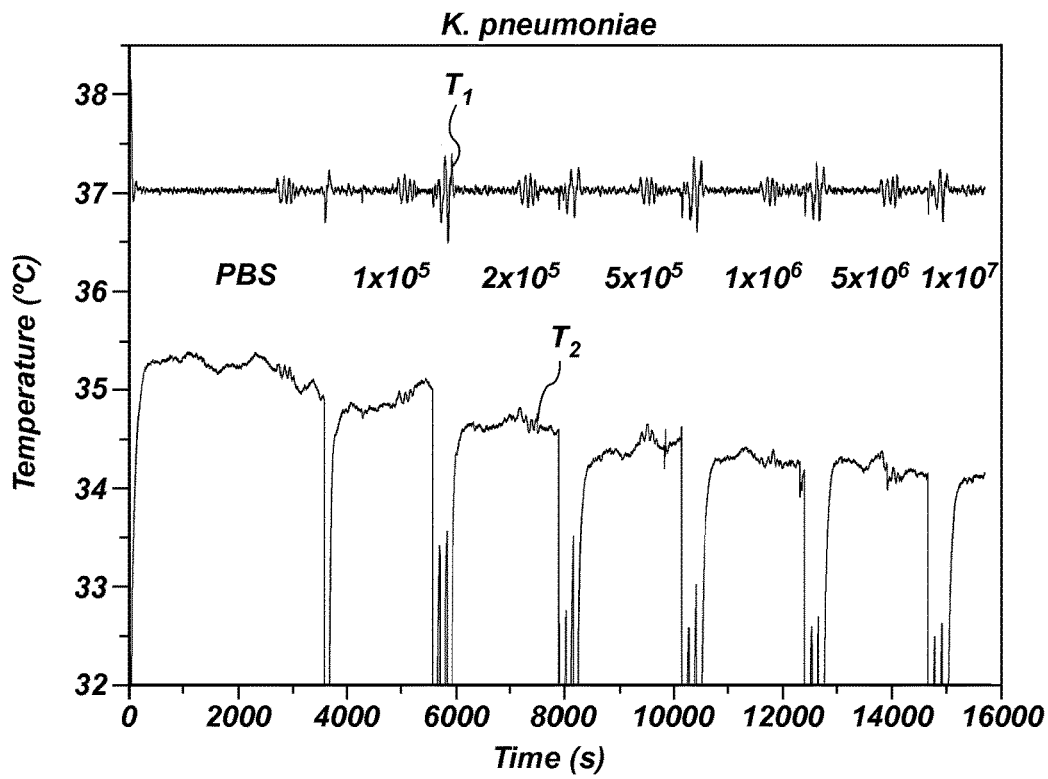
Figure 27:
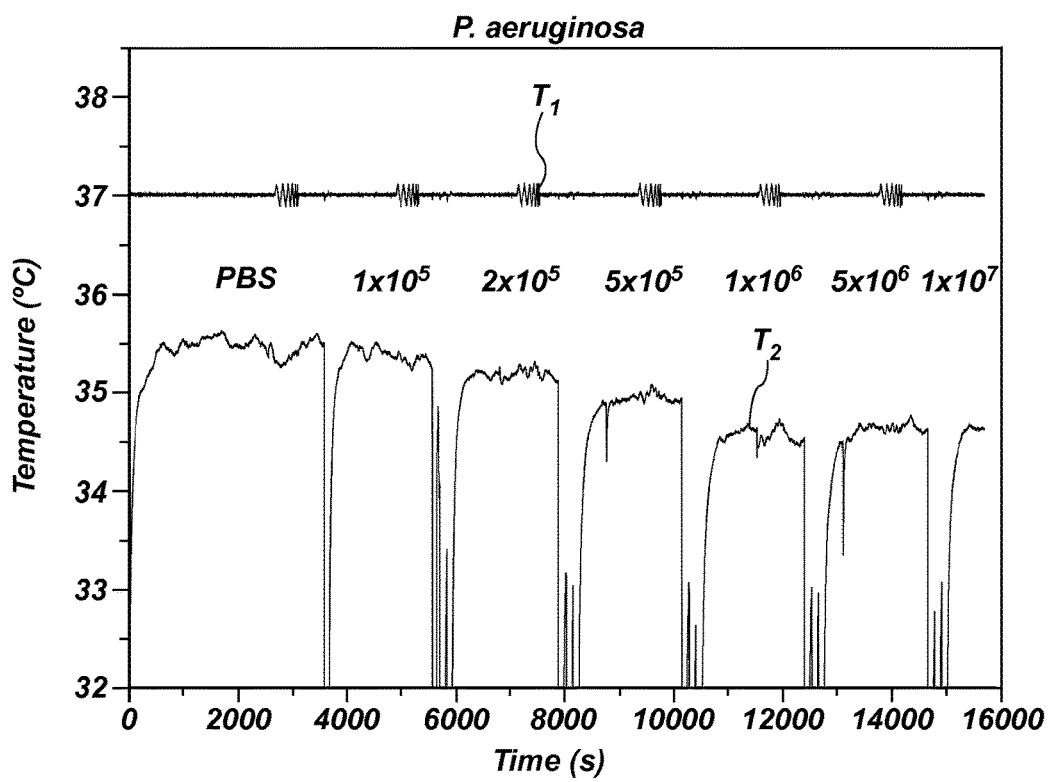
Figure 28:
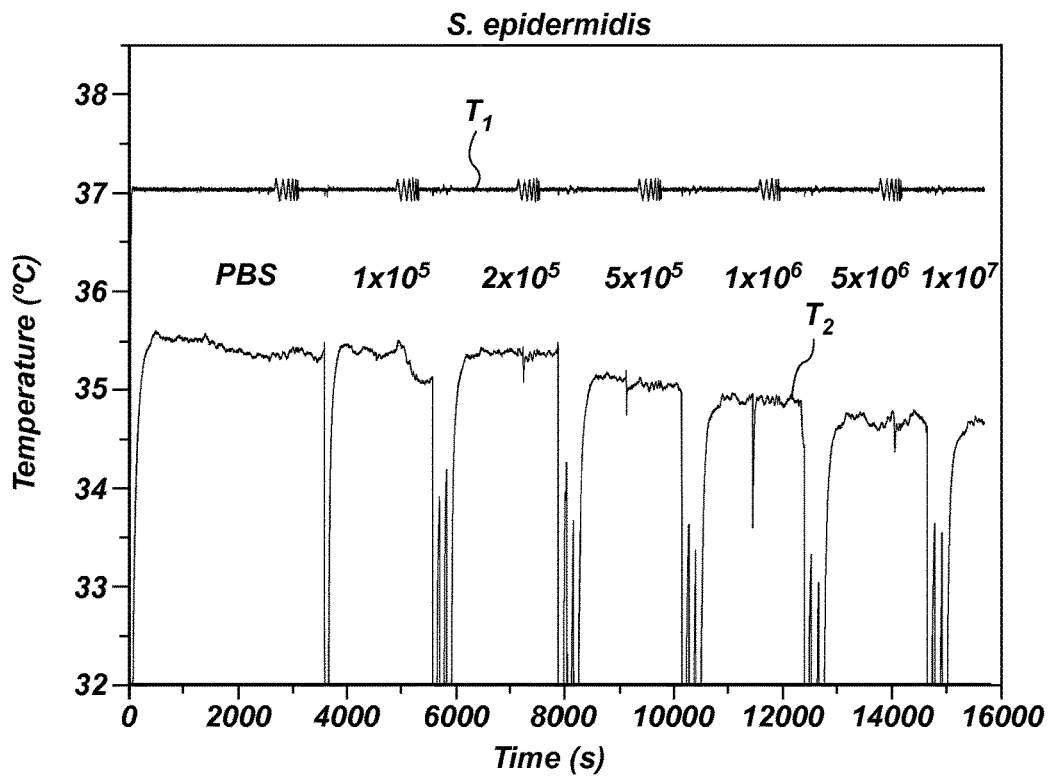
Figure 29:
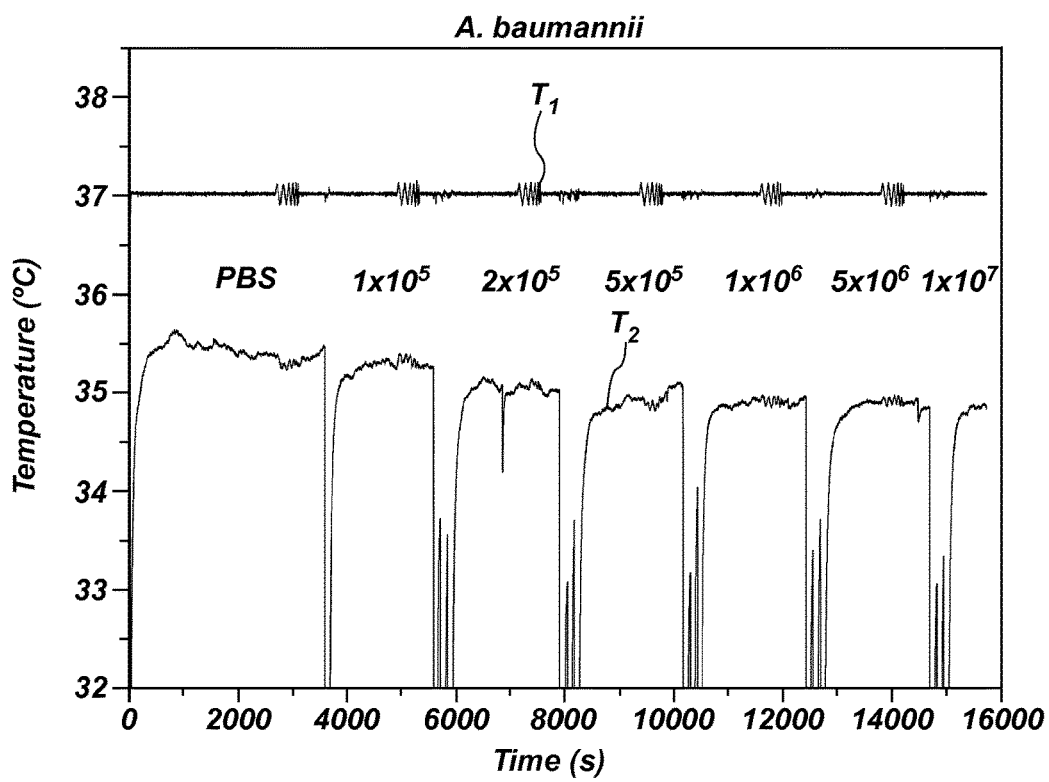
Figure 30:
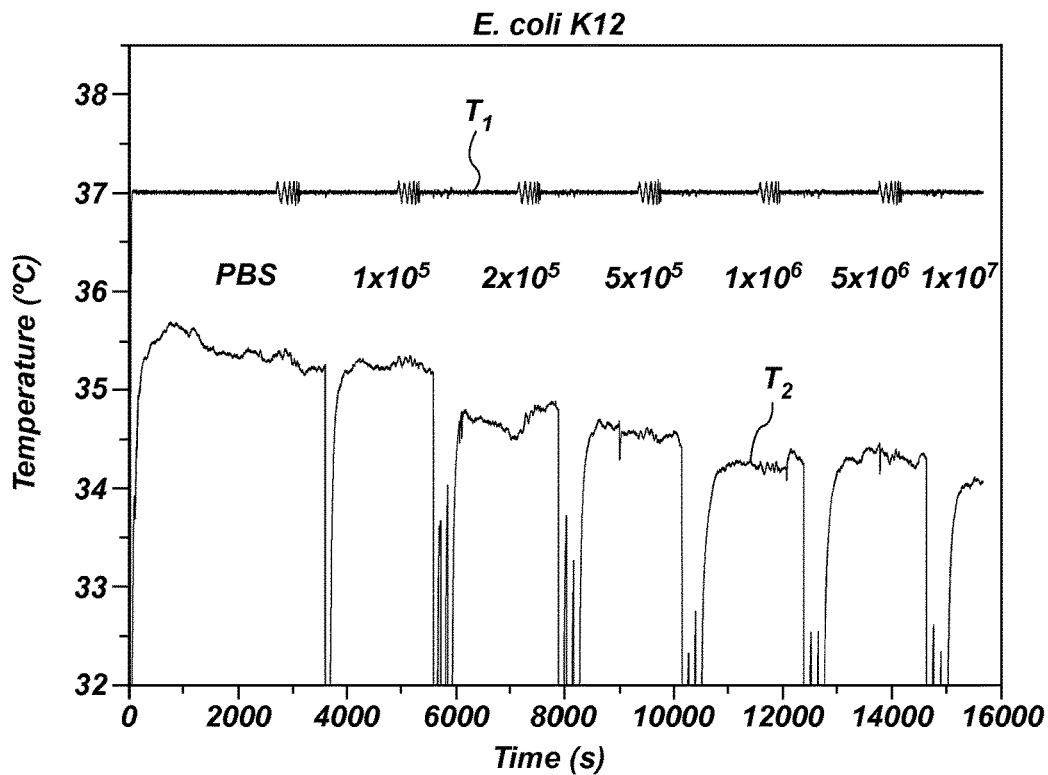
Figure 31:
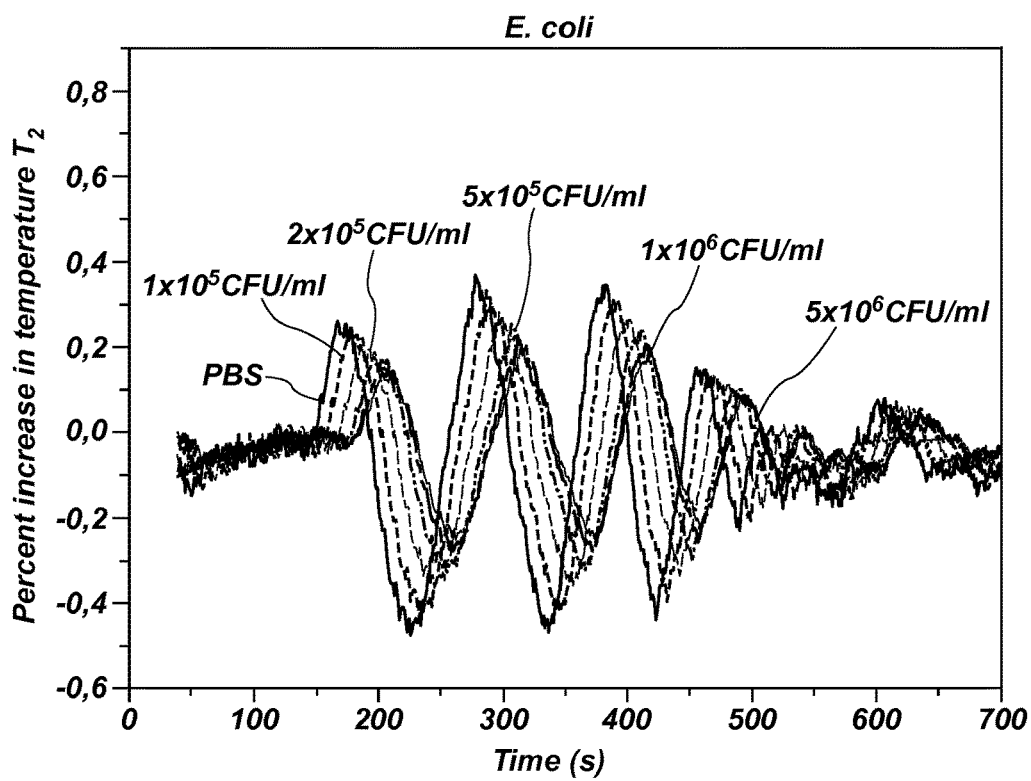
FIGS. 31 through 37 are graphs showing thermal waves measured after passing through substrates according to an embodiment of the disclosure.
Figure 32:
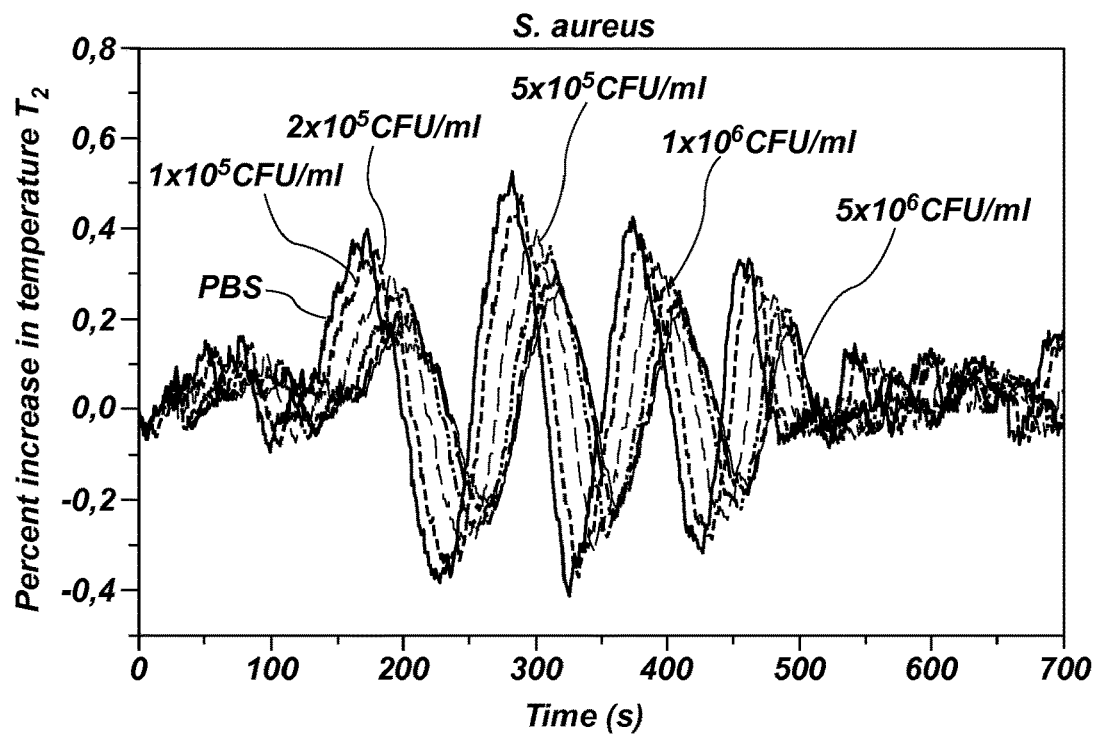
Figure 33:
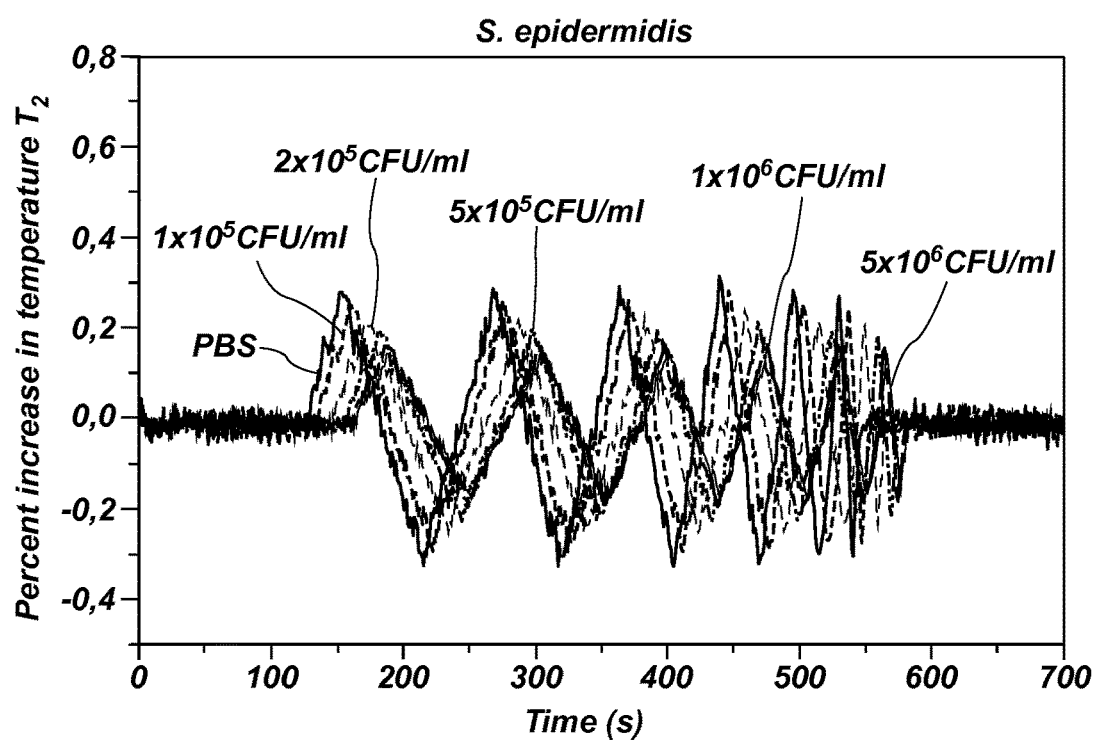
Figure 34:
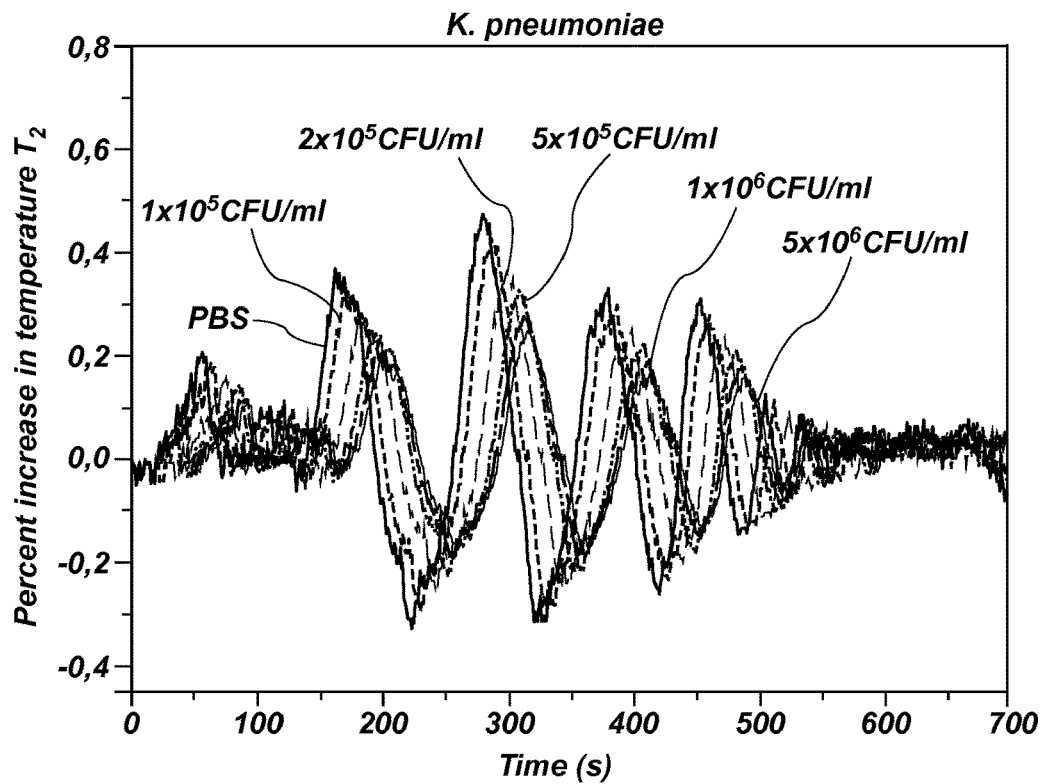
Figure 35:
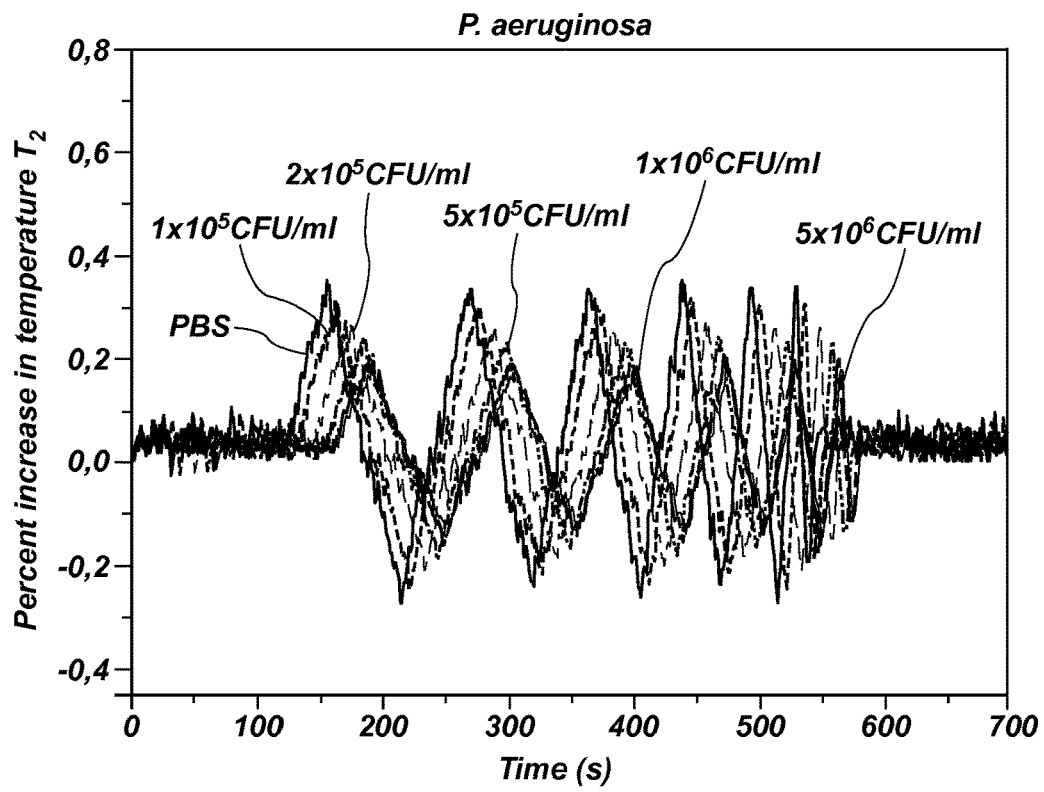
Figure 36:
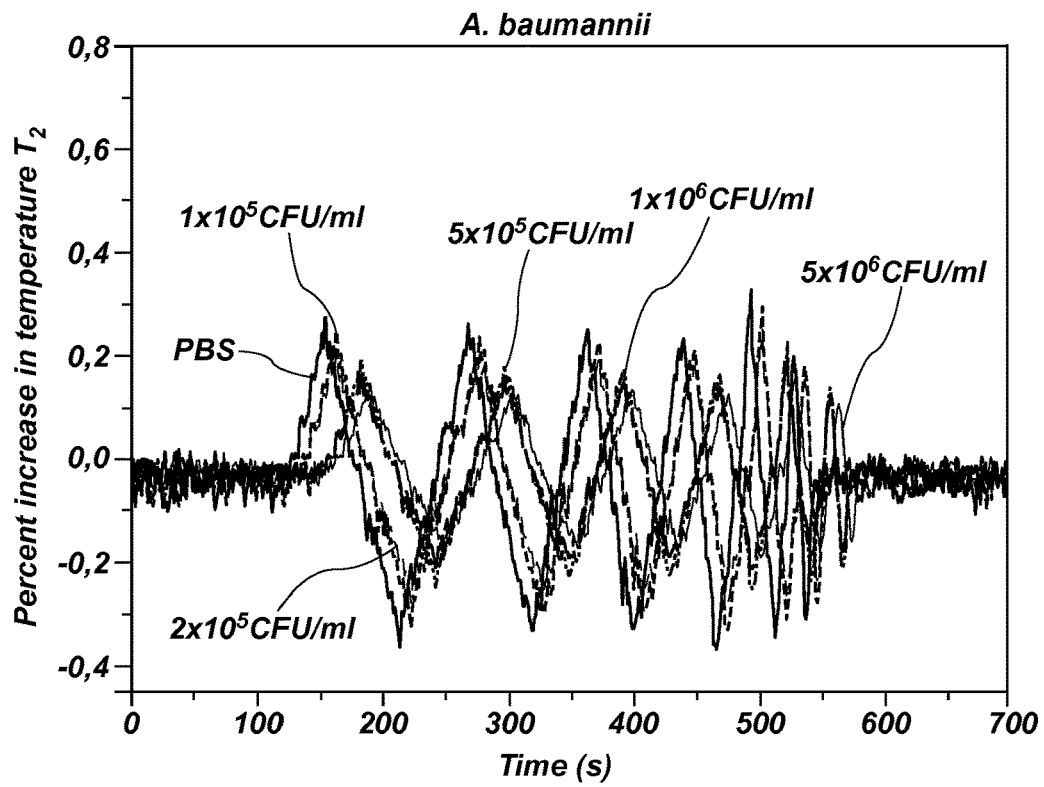
Figure 37:
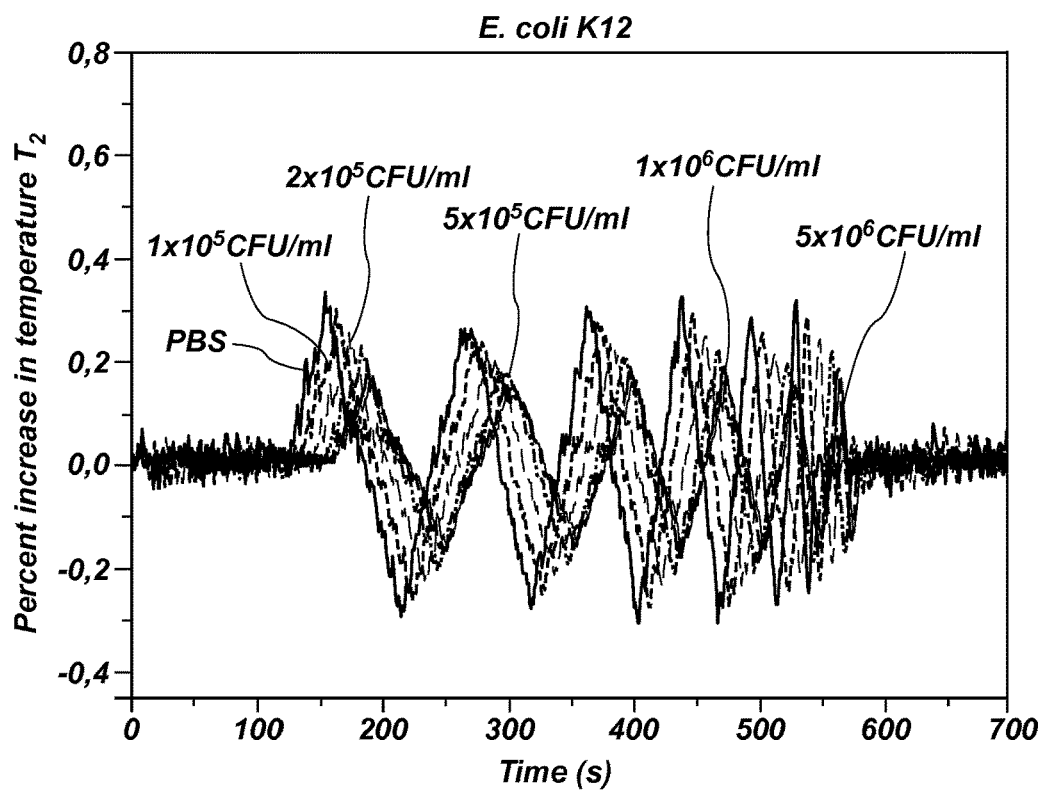

A SIP-coated substrate was imprinted with *E. coli*, as described in Example 9. The substrate was exposed three consecutive times to the mixture, and the substrate was flushed with buffer between each exposure event. The results are shown in FIG. 23, and indicate that the signal ($R_{th}$) does not significantly increase in comparison to the baseline after the first exposure event. $R_{th}$ increases after the second and third exposure steps. After exposure to the bacteria mixture, the $R_{th}$ signal initially increased to saturation.

The saturation level at each step (indicated using the scale on the right of FIG. 23) was determined as the ratio of $\Delta R_{th}$ after exposure to the mixture and after flushing with buffer respectively. The LoD is illustrated as a dashed line and is defined as three times the standard deviation on the signal, corresponding to 26.4%. After the first two cycles, the signal only reaches 0.8±8.1% and 11.8±7.8%, well below the detection limit. After a third exposure round, the signal exceeds the limit of detection at a saturation level of 32.1±8.0%

Without being bound to any particular theory, it appears that both target and analogue cells bound to the SIP-coated substrate in the first exposure. After flushing, the signal fell back to a value that did not significantly differ from the baseline value. The total concentration of target cells (*E. coli*) in the mixture was only 1×10$^5$ CFU/mL, which is below the LoD determined in Example 14. Moreover, the *E. coli* cells were outnumbered 99:1 by *S. aureus* cells, an analogue bacteria that also bind to the microcavities in the SIP-coated substrate. *E. coli* cells cannot bind to microcavities that are already occupied by *S. aureus* cells. The analogue bacteria may also prevent the target bacteria from interacting with the SIP-coated substrate, due to steric hindrance.

These problems may be at least partially overcome by increasing the number of exposure cycles. With each cycle, the signal appeared to saturate and eventually reach the LoD, indicating that enrichment may improve the sensitivity of the SIP-coated substrate and may enable it to detect lower concentrations of bacteria in increasingly complex mixtures.

Example 16: Thermal Wave Analysis to Detect Bacterial Species

Seven bacteria-imprinted polyurethane layers selective to *E. coli, S. aureus, K. pneumoniae, P. aeruginosa, S. epidermidis, A. baumannii*, and *E. coli* K-12 were formed as described in Example 9. The polyurethane layers were placed on aluminum substrates in flow cells as described in Example 10. The flow cells were each configured to vary the temperature $T_1$ of the copper block a function of time.

Each substrate was subjected to increasing concentrations of target bacteria in buffer solution. For each concentration of target bacteria, the temperature $T_1$ was kept constant for a period of time, then varied to apply a thermal wave. The temperature under the substrate was kept constant at 37° C. by applying power P. The temperature $T_2$ of the liquid flow cell was monitored in time. The thermal resistance (i.e., $R_{th}=(T_1-T_2)/P$) was also monitored over time. The results are shown in FIGS. 24 through 30.

These results show that the temperature ($T_2$) in the liquid flow cell decreases when the amount of target bacteria in the flow cell increases. This appears to indicate that bacteria are binding to the polyurethane on the substrate, increasing the thermal resistance ($R_{th}$) at the solid-liquid interface, which in turn causes $T_2$ to drop.

The thermal waves at each concentration were analyzed, and are shown in FIGS. 31 through 37. The relative change in $T_2$ was determined for each wave and the results were plotted in time, relative to the input wave.

The data in FIGS. 31 through 37 show that increasing the concentration of target bacteria in the flow cell leads to a phase shift in the thermal wave transmitted through the substrate and a decrease in amplitude of the thermal wave. Without being bound to any particular theory, it appears that as bacteria bind to the polyurethane over the substrate, the thermal resistance at the interface increases, inhibiting thermal energy to transfer to the liquid. This can be seen from the amplitude change of the wave. Additionally, the thermal wave dissipates slower over the chip resulting in the observed phase shift. The phase shift and/or amplitude change can be linked to the concentration of bacteria in the sample, and may be used to characterize the sample.

Example 17: Selectivity of Imprinted SIPs to Bacteria

Seven bacteria-imprinted polyurethane layers selective to the bacteria, identical to those tested in Example 16, were used for a cross-selectivity test. In addition, other SIPs were imprinted with *C. difficile* and *E. cecorum*, such that nine total substrates could be tested.

In order to determine the selectivity of the substrates, each of the SIPs was consecutively exposed to eight analog bacteria and finally, the target (i.e., the bacteria with which it had been imprinted) in a flow cell as described in Example 10. At each exposure step, a bacterial suspension in PBS (pH 7.4, concentration $1 \times 10^7$ CFU/mL) was injected into the flow cell. For each bacteria, the temperature $T_1$ was kept constant for a period of time, then varied to apply a thermal wave. The temperature under the substrate was kept constant at 37° C. by applying power P. The temperature $T_2$ of the liquid flow cell was monitored in time. The thermal resistance (i.e., $R_{th}=(T_1-T_2)/P$) was also monitored over time. Upon stabilization of the signal, the SIPs were flushed with buffer solution to remove any unbound material. The process was repeated until each bacteria had been tested of the eight analog bacteria, and finally, with the target.

Figure 38:
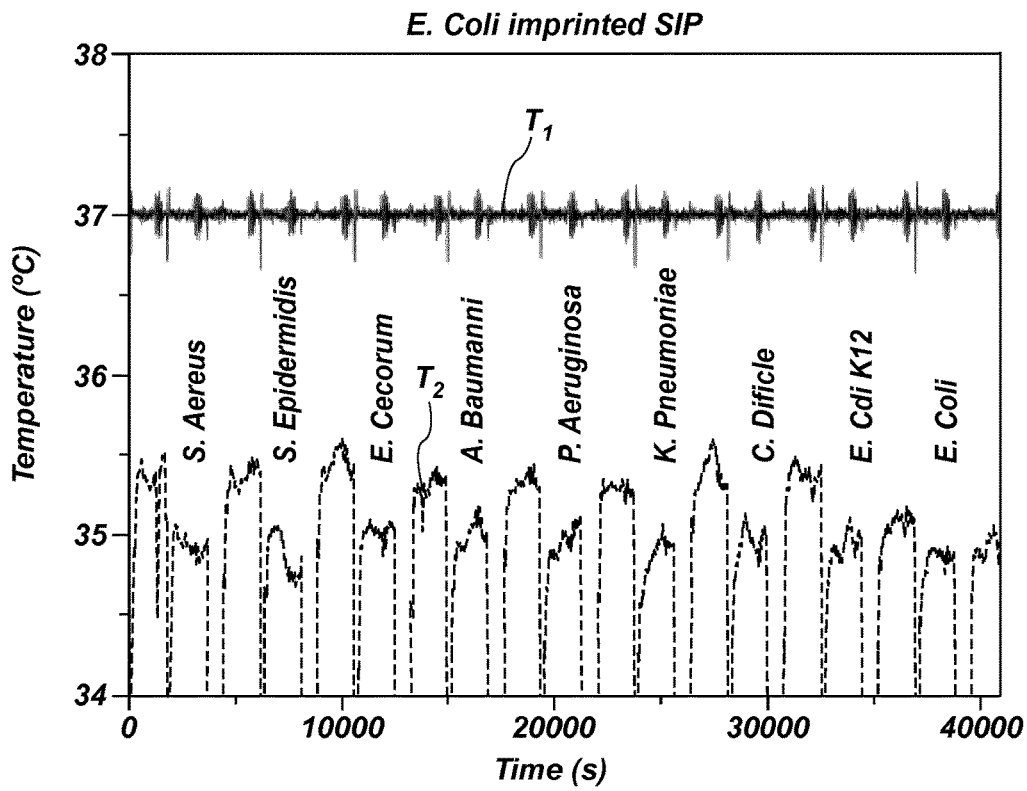
FIGS. 38 and 40 are graphs showing changes in temperature of devices when exposed to analogue and target bacteria, as measured according to embodiments of the disclosure.

The time-dependent temperature profile and TWTA analysis for an *E. coli* SIP are shown in FIG. 38. These results show that the temperature ($T_2$) in the liquid flow cell decreases when the amount of target bacteria in the flow cell increases. This appears to indicate that bacteria are binding to the polyurethane on the substrate, increasing the thermal resistance ($R_{th}$) at the solid-liquid interface, which in turn causes $T_2$ to drop. When the substrate is flushed with PBS, the bacteria—other than the target—tend to be washed away.

Figure 39:
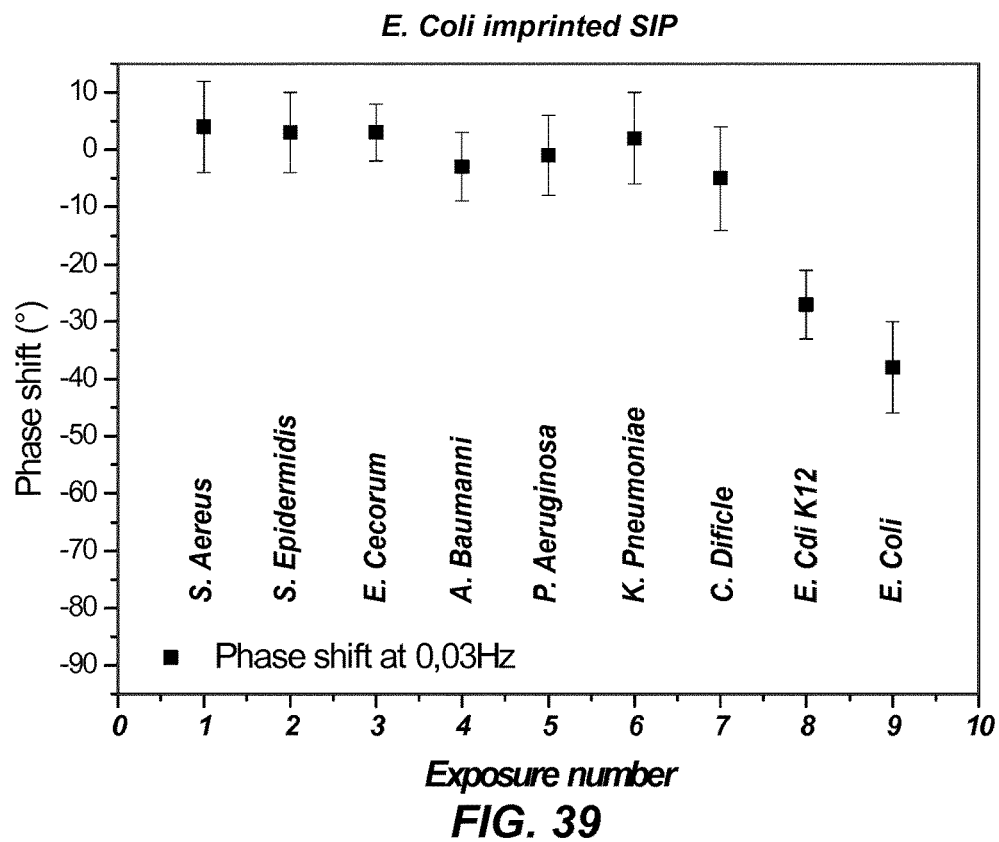
FIGS. 39 and 41 are graphs showing phase shifts at 0.03 Hz for the data depicted in FIGS. 38 and 40, respectively.

The addition of analogue cells to the flow cell leads to a decrease in $T_2$, which can be readily reversed by flushing with buffer, which corresponds to the results of Example 13. However, upon addition of *E. coli* K-12 cells, the signal does not fully return back to baseline and stabilizes at an intermediate value. Addition of target *E. coli* cells further decreases the signal to a minimum, after which the signal stays constant upon flushing with buffer. These findings are confirmed by TWTA. FIG. 39 shows the phase shift at 0.03 Hz for the TWTA test for each of the bacteria on the *E. coli* imprinted SIP. The first seven analogue bacteria do not cause a phase shift in the transmitted wave compared to the input wave, but exposure to both the analogue *E. coli* K-12 and the target *E. coli* cells results in a measurable phase shift with a maximum being observed for *E. coli* cells.

Figure 40:
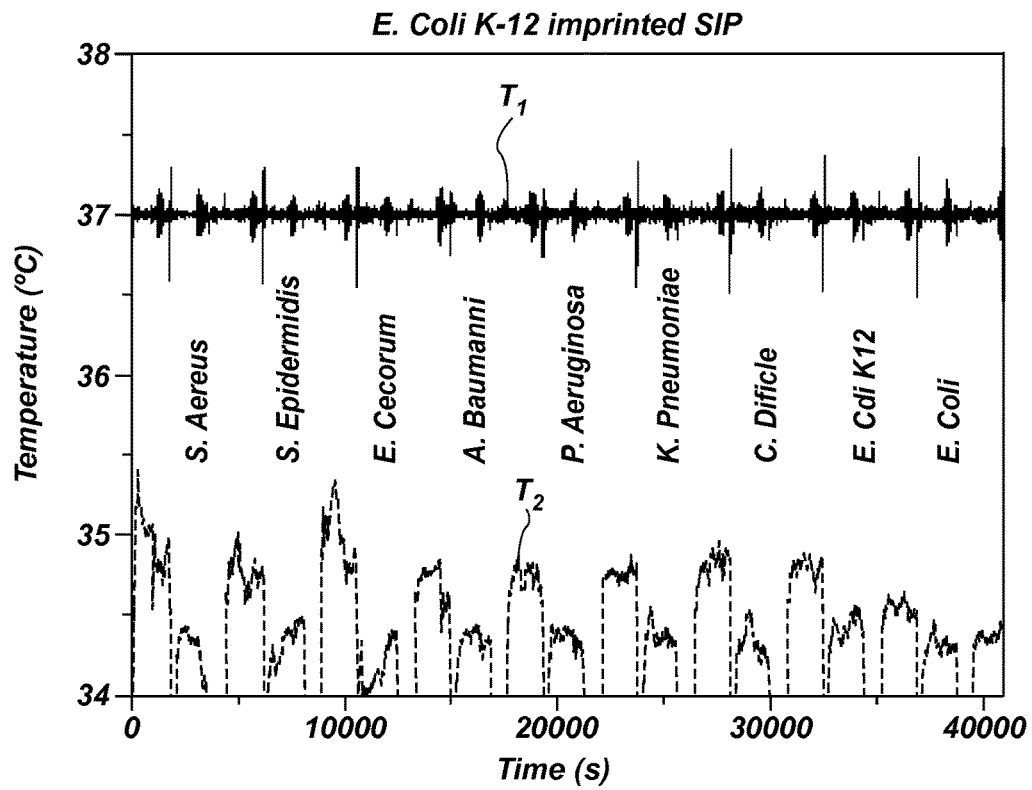
Figure 41:
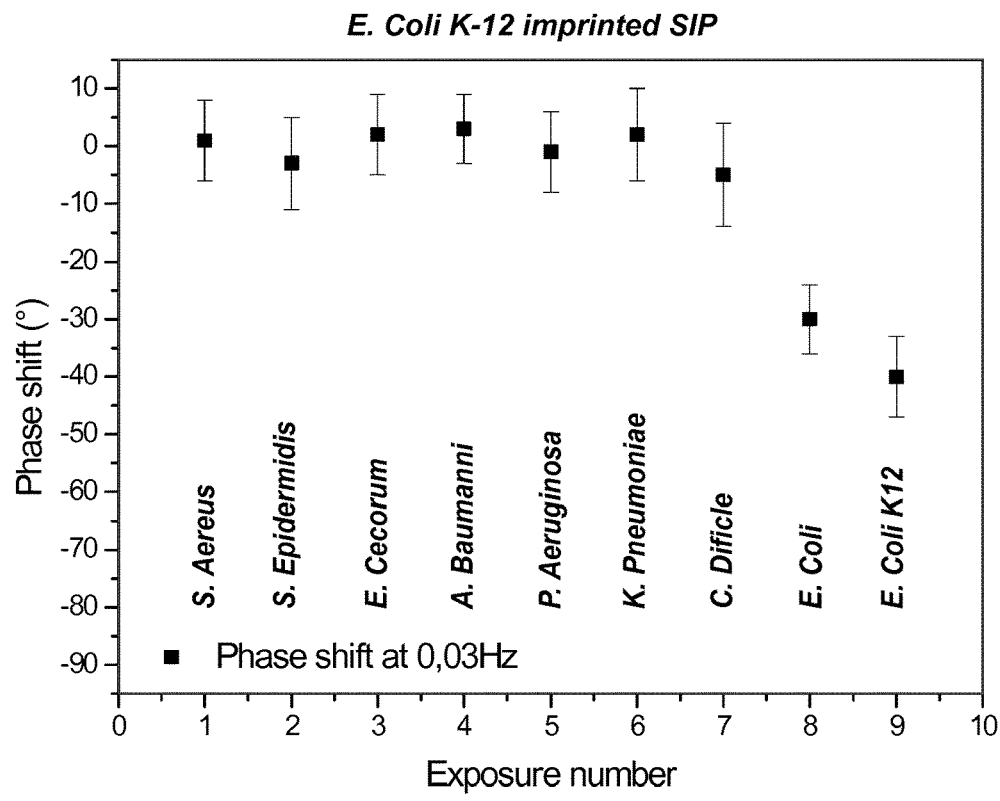

A similar experiment on an *E. coli* K-12 imprinted SIP confirms these results, as shown in FIGS. 40 and 41. In addition to these experiments, SIPs were imprinted for each of the bacteria under study and exposed consecutively to target and analogue bacteria. The data indicate that no cross-selectivity is observed in similar experiments using these SIPs. The results of these experiments are summarized in Table 2.

TABLE 2

Cross-selectivity of SIPs imprinted with different bacteria

| SIP | Target | | | | | | | | |
|---|---|---|---|---|---|---|---|---|---|
| | A. b. | K. p. | S. e. | S. a. | C. d. | E. cec. | P. a. | E. c. K-12 | E. c. |
| A. baumannii | S | none | none | none | none | none | none | none | none |
| K. pneumoniae | none | S | none | none | none | none | none | none | none |
| S. epidermidis | none | none | S | none | none | none | none | none | none |
| S. aureus | none | none | none | S | none | none | none | none | none |
| C. difficile | none | none | none | none | S | none | none | none | none |
| E. cecorum | none | none | none | none | none | S | none | none | none |
| P. aeruginosa | none | none | none | none | none | none | S | none | none |
| E. coli K-12 | none | none | none | none | none | none | none | S | NS |
| E. coli | none | none | none | none | none | none | none | NS | S |

S = specific cell binding,
NS = non-specific cell binding,
none = no cell binding The results described in Example 17 indicate that a sensor platform having one or more imprinted SIPs may selectively discriminate between various types of bacteria in buffer in a quantitative manner.

Example 18: Selectivity of Imprinted SIPs when Exposed to a Complex Mixture

A sample encountered during on-site bacterial detection and identification might be expected to contain an excess of competitor molecules and cells in addition to a trace amount of the target. In an attempt to simulate this condition, a SIP imprinted with *S. aureus*, as described in Example 9, was selected for a progressive enrichment experiment exposing the SIP to a mixture of bacteria. A mixture of the nine bacteria tested in Example 19 was prepared, containing *S. aureus* and an excess of the eight non-target bacteria. The ratio of *S. aureus* to each of the non-target bacteria was 1:99, and the total concentration of bacteria was $1 \times 10^7$ CFU/mL. The SIP was exposed to the mixture five consecutive times, and was flushed with buffer (PBS) between each of the exposure events.

Figure 42:
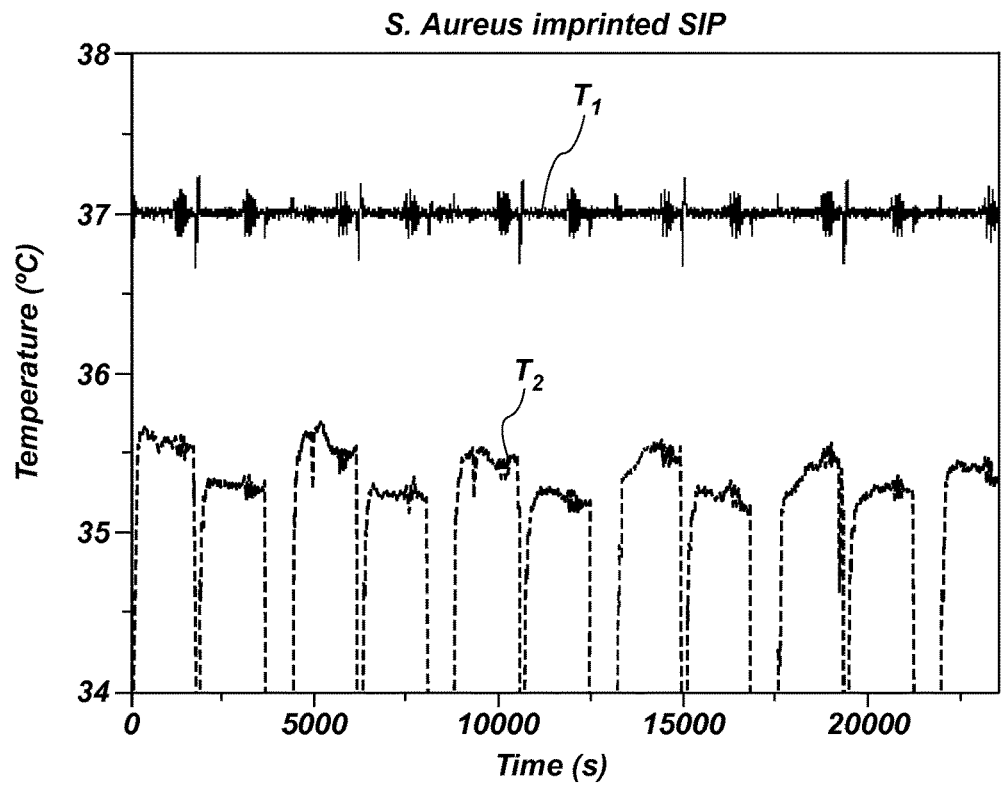
FIG. 42 is a graph showing changes in temperature of a device as measured during repeated exposure to a mixture of bacteria, according to embodiments of the disclosure.

The time-dependent temperature profile is shown in FIG. 42. In order to validate TWTA as a measuring technique for SIP-based bacteria detection, HTM was used as a reference technique. Therefore, the thermal resistance $R_{th}$ was calculated from the temperature profile according to Equation 2 (see Example 5).

Figure 43:
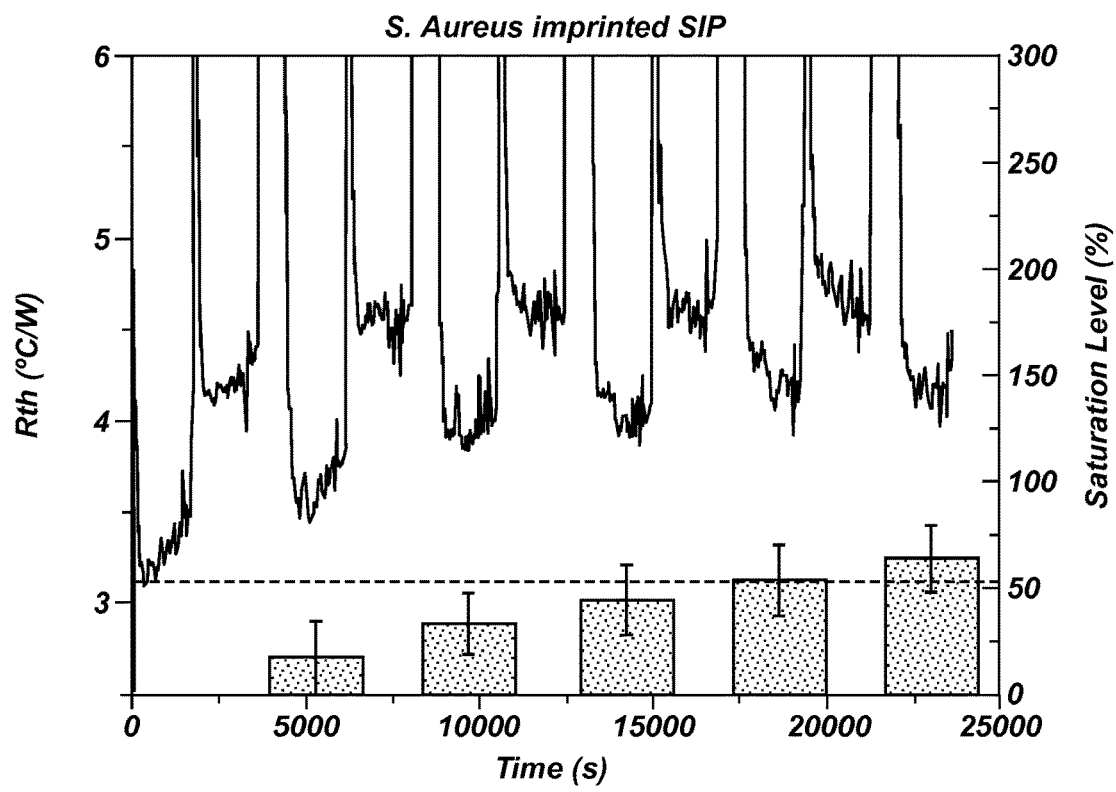
FIG. 43 is a graph showing thermal responses of the device for which the temperature changes are shown in FIG. 42, as well as a boxplot summarizing the thermal responses.

The thermal resistance data are shown FIG. 43, simplified by applying a median filter as a guide to the eye. To visualize the effect of progressive enrichment more clearly, the saturation level of the $R_{th}$ response was calculated for each exposure cycle (consisting of cell exposure followed by flushing) by dividing the net effect size after flushing by the maximal effect size upon addition of the mixture to the flow cell. These results indicate that the net signal gradually increases with each exposure cycle until the limit-of-detection is reached after four-to-five exposure cycles. The limit-of-detection value is indicated as the dashed line in FIG. 43, and is defined as three times the maximal error on the $R_{th}$ signal throughout the measurement (i.e., the 3σmethod).

Figure 44:
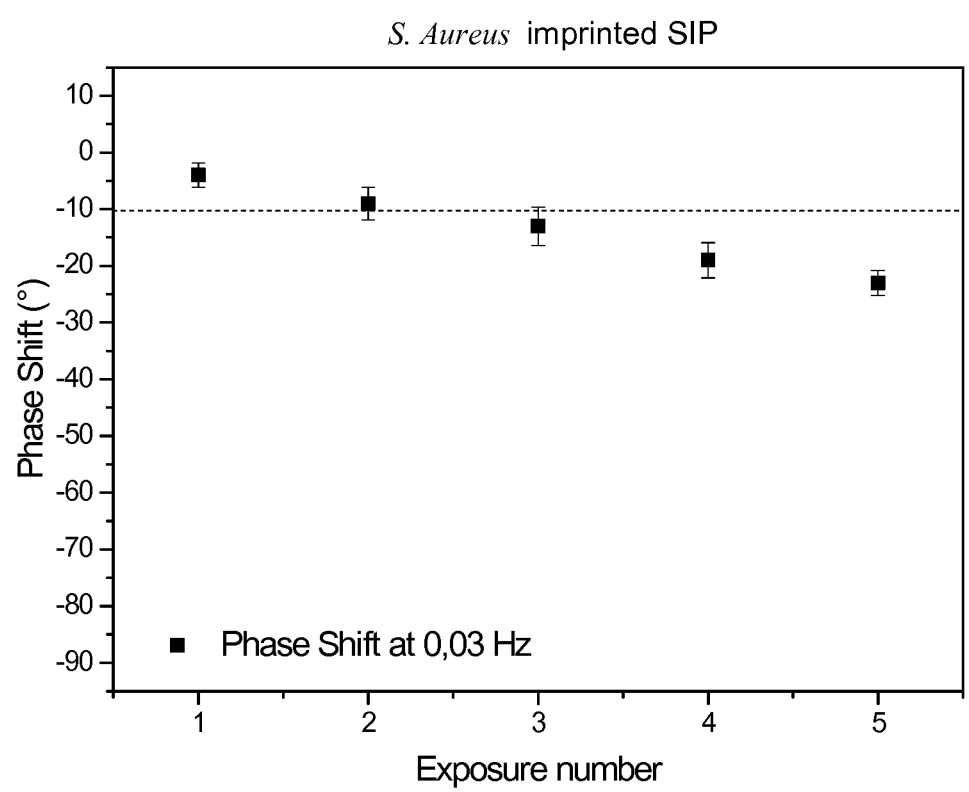
FIG. 44 is a graph showing phase shift at 0.03 Hz for the data depicted in FIG. 42.

The TWTA data, depicted in FIG. 44, show a similar trend. The net phase shift observed in the transmitted wave after each exposure cycle increases gradually and after the third exposure cycle, the signal reaches the limit-of-detection.

Due to the excess of competitor bacteria in the mixture, it appears that only a small amount of target bacteria can bind to the SIP. Therefore, both the responses in thermal resistance $R_{th}$ (FIG. 43) and phase shift (FIG. 44) are less pronounced than they would be when exposed to only the target bacteria. As the number of exposure events increases, the response gradually increases and eventually reaches the limit-of-detection level apparently because the non-target bacteria are washed from the SIP, exposing binding sites free to accept target bacteria on the next cycle. Because the noise on the signal for HTM is significantly higher, the LoD for HTM is only reached after four or even five consecutive cycles, whereas a measurable signal that can be regarded as significant is already apparent after two-to-three cycles when using TWTA as a measurement technique. It appears that because of the low amount of noise on the thermal wave, the development of the TWTA principle can be considered as a valuable advance in thermal bacterial identification.

It has been unexpectedly discovered that the methods and devices described herein may be used to discriminate not only between strains of similar bacteria, but also between living and dead bacteria of the same strain. Without being bound to any particular theory, it appears that the difference in surface chemistry between living and dead *E. coli* is sufficient to discriminate between them, despite their morphological similarities.

Furthermore, it has been unexpectedly discovered that rinsing non-target analytes (e.g., bacteria similar but not identical to a target analyte bacteria) can increase the detection capability of a polymer material by freeing binding sites of non-target analytes without removing target analytes from other binding sites. Thus, binding sites that were initially occupied by target analytes may remain filled, and binding sites that were initially occupied by non-target (but analogue) analytes may be cleared for re-binding with another analyte (in particular, with the target analyte). Analogue bacteria may bind to imprints to some extent, possibly due to the presence of bacteria-specific functional groups on the membrane of the cells that are compatible to some of the functional groups inside the imprints. However, the bond does not appear to withstand shear forces provided by flushing. The target bacteria, on the other hand, appear to remain firmly bound to the polymer, such that the thermal resistance remains at an elevated level even after flushing. Such clearing and re-binding may be useful for characterizing complex mixtures of similar or related analytes because related analytes may tend to weakly bind to sites imprinted for one another. By clearing and re-binding analytes, lower concentrations of the target analyte may be detected.

The methods and devices described herein may be used in conjunction with steady-state or thermal-wave analysis techniques. Various shapes of substrates may be used, and data (e.g., temperature) may be collected at various points, such as in the liquid to be analyzed, in a substrate coated with polymer material, or in a coated thermocouple.

Methods described herein may be used to provide real-time or nearly real-time characterization of bacteria that is conventionally performed in laboratories having complex equipment and highly trained personnel. Thus, the methods and devices may enable faster and cheaper data collection, and may enable improved outcomes by, for example, identifying bacterial outbreaks within a population. Such methods may be beneficial in health care, environmental and food safety (e.g., by detecting water-, air-, and food-borne bacteria), and counter-terrorism (e.g., by detecting anthrax, etc.).

The invention claimed is:

1. A device for detecting an analyte, the device comprising:
    a substrate having a polymer material formed on a surface thereof, the polymer material formulated to bind to the analyte, wherein a heat transfer property of the polymer material is formulated to vary based on an amount of the analyte bound thereto;
    a heat transfer element thermally coupled to a surface of the substrate opposite the polymer material;
    a temperature modification device thermally coupled to the heat transfer element;
    a controller configured to cause the temperature modification device to produce a thermal wave emanating from the heat transfer element;
    a flow cell located and configured to pass a liquid over the polymer material of the substrate;
    a temperature sensor configured to detect a temperature of the liquid passing over the polymer material; and
    a processor configured to calculate a concentration of an analyte in the liquid based at least in part on a phase shift between the thermal wave at the heat transfer element and an attenuated thermal wave in the liquid.

2. The device of claim 1, wherein the heat transfer element comprises copper.

3. The device of claim 1, wherein the controller is configured to change a temperature of the heat transfer element at a variable frequency.

4. The device of claim 1, wherein the polymer material comprises an imprinted polymer.

5. The device of claim 1, wherein the polymer material comprises a material selected from the group consisting of DNA, RNA, proteins, and portions and analogs thereof.

6. The device of claim 1, wherein the polymer material is formulated to bind to a first bacteria with a first affinity higher than a second affinity of the polymer material to a second bacteria.

7. The device of claim 6, wherein the first bacteria comprises living bacteria, and wherein the second bacteria comprises dead bacteria, the living bacteria and the dead bacteria being of the same species.

8. The device of claim 6, wherein the first bacteria comprises a first species, and wherein the second bacteria comprises a second species, the second species being an analogue of the first species.

9. A method for detecting an analyte, the method comprising:
passing a liquid containing an analyte over a polymer material on a substrate, the polymer material formulated to bind to the analyte, wherein the polymer material is formulated such that the polymer material varies based on an amount of the analyte bound thereto;
binding the analyte to the polymer material;
providing a thermal wave from a heat transfer element to the polymer material through the substrate;
detecting a temperature of the liquid; and
calculating a concentration of the analyte in the liquid based at least in part on a phase shift between the thermal wave produced by the heat transfer element and an attenuated thermal wave in the liquid.

10. The method of claim 9, further comprising generating the thermal wave with a controller configured to change a temperature of a temperature modification device thermally coupled to the heat transfer element.

11. The method of claim 9, wherein calculating a concentration of the analyte in the liquid comprises determining a difference in amplitude between the thermal wave at the heat transfer element and the attenuated thermal wave in the liquid.

12. The method of claim 9, wherein providing a thermal wave from a heat transfer element to the polymer material through the substrate comprises changing a frequency of the thermal wave.

13. The method of claim 9, wherein calculating a concentration of the analyte in the liquid comprises calculating a concentration of histamine in the liquid.

14. The method of claim 9, wherein passing a liquid containing an analyte over a polymer material on a substrate comprises passing the liquid containing the analyte over a molecularly imprinted polymer.

15. The method of claim 9, wherein passing a liquid containing an analyte over a polymer material on a substrate comprises passing the liquid containing the analyte over a material selected from the group consisting of DNA, RNA, proteins, and portions and analogs thereof.

16. The method of claim 9, wherein providing a thermal wave from a heat transfer element to the polymer material through the substrate comprises changing a temperature of the heat transfer element by less than 0.2° C.

17. The method of claim 9, wherein calculating a concentration of the analyte in the liquid comprises calculating a concentration of living bacteria in a mixture comprising living and dead bacteria of the same species.

18. A method of forming a device for detecting an analyte the method comprising: forming a polymer material over a surface of a substrate, the polymer material formulated to bind to the analyte, wherein a heat transfer property of the polymer material is formulated to vary based on an amount of the analyte bound thereto; thermally coupling a heat transfer element to a surface of the substrate opposite the polymer material; thermally coupling a temperature modification device to the heat transfer element; configuring a controller to cause the temperature modification device to produce a thermal wave emanating from the heat transfer element; configuring a flow cell to pass a liquid over the polymer material of the substrate; configuring a temperature sensor to detect a temperature of the liquid passing over the polymer material; and configuring a processor to calculate a concentration of an analyte in the liquid based at least in part on a phase shift between the thermal wave at the heat transfer element and an attenuated thermal wave in the liquid.

19. The method of claim 18, wherein forming a polymer material over a surface of a substrate comprises screen-printing the polymer material over the surface of the substrate.

20. The method of claim 18, wherein forming a polymer material over a surface of a substrate comprises forming a molecularly imprinted polymer over the surface of the substrate.

* * * * *